United States Patent [19]

Reddy et al.

[11] Patent Number: 6,080,401

[45] Date of Patent: Jun. 27, 2000

[54] HERBAL AND PHARMACEUTICAL DRUGS ENHANCED WITH PROBIOTICS

[76] Inventors: Malireddy S. Reddy, 78 Cherry Hills Farm Dr., Englewood, Colo. 80110; Damavarapu Radha Krishna Reddy, Road No. 15, 133A, Jubilee Hills, Hyderabad, Andhra Pradesh; Naraparaju A. V. Prasad, Regn. 12-11-1393/3, Wrasiguda, Secunderabad-61, Andhra Pradesh, both of India

[21] Appl. No.: 09/196,922

[22] Filed: Nov. 19, 1998

[51] Int. Cl.[7] .................................................... A61K 35/78
[52] U.S. Cl. ................... 424/93.3; 424/93.1; 424/93.4; 424/93.44; 424/93.45; 424/93.51; 424/93.5; 424/195.1
[58] Field of Search ................. 424/195.1, 93.1, 424/93.3, 93.4, 93.44, 93.45, 93.51, 93.5

[56] References Cited

U.S. PATENT DOCUMENTS

| 5,308,615 | 5/1994 | DeLoach et al. | 424/93 C |
|---|---|---|---|
| 5,501,857 | 3/1996 | Zimmer | 424/438 |
| 5,604,127 | 2/1997 | Nisbet et al. | 435/252.4 |
| 5,709,857 | 1/1998 | Morelli et al. | 424/93.45 |
| 5,738,651 | 4/1998 | Walton et al. | 604/83 |
| 5,741,525 | 4/1998 | Larsen | 424/616 |

FOREIGN PATENT DOCUMENTS

WO 97/20577   6/1997   WIPO.

OTHER PUBLICATIONS

Jost, M., Agrarforschung, vol. 3(9), p. 451–454. Abstract, 1996.
Young, R.J. et al., Gastroenterology, vol. 114(4), pt. 2, p. A435. Abstract, Apr. 1998.
Rada, V. et al., Archives of Animal Nutrition, vol. 50(1), p. 25–29, 1997.
Bengmark, S., Nutrition, vol. 14(7/8), p. 585–594, 1998.
Harper, A.F. et al., Animal Feed Science and Technology, vol. 8(1), p. 69–76, Jan. 1983.
Hentchel, C. et al., Gastroenterology, vol. 112(4) (suppl.), p. A146, Apr. 1997.

*Primary Examiner*—Jean C. Witz
*Attorney, Agent, or Firm*—Kyle W. Rost

[57] ABSTRACT

The curative action of drugs, including herbal remedies, allopathic remedies, and periodontal remedies, is enhanced and accelerated by administering such drugs in combination or association with probiotics, especially those of genus Lactococcus, Lactobacillus, Pediococcus, Streptococcus, Propionibacterium, Brevibacterium, Penicillium, and Saccharomyces.

20 Claims, No Drawings

HERBAL AND PHARMACEUTICAL DRUGS ENHANCED WITH PROBIOTICS

TECHNICAL FIELD

The invention generally relates to bio-affecting drugs and body treating compositions. More specifically, the invention relates to drugs and compositions containing whole, live micro-organisms. In some cases, the invention further relates to intentional mixtures of two or more micro-organisms of different genera. The invention relates to pharmacotherapy in which the scope of medicinal preparations includes a range of pharmaceuticals include allopathic drugs, homeopathic drugs, and herbal drugs.

BACKGROUND ART

Herbal medicines or herbal drugs are of ancient origin and their use is known in cultures throughout the world. Chinese herbal medicine is among the earliest known examples of organized scientific study and formulation of herbal treatments. Herbalism is known to have been popular in China as early as 2500 B.C. Approximately at this same time, scripts appeared in India describing the healing powers of herbs. In India herbal medicine was termed "ayurueda" medicine, which gives us the modem term "ayurvedic," derived from "ayur," meaning life and "veda" meaning knowledge. In other words, ayurvedic medicine is regarded as derived from "knowledge of life," which reflects the empirical growth of herbalism as different natural products were found useful in treating human or animal ailments.

The practice of herbal medicine spread from Asia to Europe. The Greeks are known to have acquired knowledge of it over the period from 468–377 B.C. In turn, the Romans learned of it from the Greeks around 100 B.C. The Islamic world learned of and began to practice this science around the time the Roman Empire fell, in the 5th century. By the 10th century, the Anglo-Saxon world was practicing herbal science and describing it in writings. Throughout the middle ages, most herbalism was practiced under the authority of the church, which maintained the authority to grow medicinal herbs and to introduce new herbal medicines. Church control of herbalism continued despite the origin of several medical schools in the later middle ages.

European settlers brought herbal medicine with them to North America Perhaps not surprisingly, they found that Native Americans also used herbs to cure diseases. An early colonial New Hampshire herbalist, Samuel Thompson, integrated Native American and European herbal practices of the day. During the early 19th century, Thompson's theories on botanical practices of medicine were well recognized, and literature reports that three million people were following Thompson's principles.

A movement to identify individual active ingredients in beneficial herbs developed in the 18th century, leading into a transitional period from the use of natural herbs to the use of pharmaceutical drugs such as extracts and purified chemicals, sometimes referred to as allopathic drugs. With advances in chemistry, some of the active ingredients were chemically synthesized and given to patients in the form of pills. However, during this time of transition, the synthesized, purified or extracted active ingredients of pharmaceutical drugs first were observed to exhibit significant adverse side effects. Generally, herbal medicines do not produce significant side effects, perhaps because the active ingredients are combined with other compounds in the herb and administered in different dosages. In addition, herbs often are administered in combinations, which may nullify the side effect of any one herb. However, purified pharmaceutical drugs seldom are administered in combinations to offset each other's side effects, perhaps because even the offsetting drug is likely to produce its own side effects. It appears that modern medical practice accepts the presence of side effects as an adjunct to the improved purity and efficacy of pharmaceutical drugs. The notoriety of this problem is indicated by the industry-wide practice of providing data sheets with disclosure of known side effects, negative indications, and other cautions with substantially every allopathic drug, whether of the type requiring doctor's prescription or sold over-the-counter. Modern drug synthesis has the advantages of providing pure and potent drugs in large quantities and with considerable speed for wide availability. However, the accompanying problem of side effects is gaining increased notice as the public justly criticizes that such pure and potent drugs can cure one ailment while causing another.

As an example of an herbal remedy that led to a synthesized drug, in 1852 the artificial synthesis of salicin was considered to be a major advancement. Salicin is an active herbal ingredient found in willow bark. The Bayer Company launched the commercial sale of synthesized acetyl salicylic acid under the trademark, Aspirin, 1899. The pure acetyl salicylic acid commonly is known to be potent and effective, although possible side effects such as digestive upset and kidney damage are equally well known, although not observed in the days when the drug was administered via willow bark.

Other active herbal compounds have been extracted and chemically synthesized for use in the modern allopathic medical practice, with similar result. For example, Indian snake root, also known as *rauwolfia serpentina*, has been used in Indian ayurvedic medicine for centuries to cure anxiety, headaches, and high blood pressure. In 1947, the alkaloid, reserpine, was extracted from snake root and sold by Ciba Company to treat hypertension. Although the pure extract, reserpine, does reduce hypertension, it also exhibits adverse side effects such as severe depression and abnormal slowing of the heart beat. Such side effects were not seen when natural snake root was ground and administered to achieve similar beneficial results.

A significant problem with herbal medicine is that herbs are slow acting in treating an ailment In contrast, allopathic drugs act comparatively quickly. For this reason, medical practice prefers allopathic drugs as the effective means of treatment, even though the drugs have side effects. Clearly, it would be desirable to increase the speed by which herbal medicines act, but while maintaining the natural, herbal character of the medicine so as to avoid or minimize harmful side effects. An increasing number of people are gaining awareness of the advantages of herbal medicine together with a concern over the disadvantages of modern purified drugs. Consequently, there has been an increasing public interest in the use herbal medicines or ayurvedics, although the slowness of treatment remains a problem. Thus, many people consider herbs primarily useful as a maintenance or prophylactic treatment to be taken regularly in order to prevent onset of illness. A faster acting type of herbal medicine would create far broader utility.

Probiotics are bacteria or micro-organisms that are beneficial to the health of an individual. They are essentially an opposite of antibiotics, which are inhibitory to other bacteria, including probiotic bacteria. Probiotics are predominately lactic acid producing bacteria. In contrast to herbal medicine, probiotics developed as a science only recently; and this science remains unacknowledged by many medical practitioners. One of the earliest discoveries that bacteria can improve human health was by Dr. Metchnikoff, a Russian scientist, in 1907. Since then, there have been favorable reports about probiotics' utility, including, for example, that *lactobacillus acidophilus* reduces colon cancer in humans. Also, Russian scientists have reported that daily ingestion of *lactobacillus bulgaricus* and *streptococcus thermophilous* can improve human longevity. Several American scientists have reported that the level of blood cholesterol in humans can be reduced by orally ingesting *lactobacillus acidophilus*. These probiotic organisms are believed to exhibit therapeutic effects because of their innate ability to produce lactic acid and other substances that are inhibitory to harmful bacteria. These probiotic organisms naturally reside in the human intestinal tract, at receptor sites in the ileum (distal end of small intestinal tract) where they create a mildly acidic environment.

Probiotics are widely present in nature and serve many beneficial functions. Biologically, they are classified as plants. They are non-pathogenic, do not produce toxins, and are considered natural and organic. The U.S. Food and Drug Administration has granted them GRAS (generally regarded as safe) status. They can be used in food preparation safely and are used extensively in the manufacture of dairy products such as yogurt, buttermilk, sour cream, and cheeses. They are used in dairy products primarily to preserve milk over a long period of time due to their ability to digest sugars and produce beneficial organic acids. They also make these food preparations flavorful. Probiotic organisms also have been used to improve the health of young animals such as calves and baby pigs.

These beneficial bacteria have an antagonistic effect on pathogenic bacteria, while antibiotics have an antagonistic effect on probiotics. Consequently, when a person is treated with antibiotics, the probiotics residing in the gastrointestinal tract can be killed, adding another complexity to the illness. To counteract this problem, some physicians prescribe the use of probiotics following use of an antibiotic in order to restore healthy gastrointestinal flora Some drug manufacturers combine probiotics and antibiotics, although such combinations may be poorly advised due to the inherent conflicting purposes of the two types of microorganisms. One danger is that such combination may produce antibiotic resistant bacteria, which later might pass this characteristic to a pathogenic bacteria which no longer could be inhibited by that specific antibiotic.

It would be desirable to more widely employ natural agents such as herbal mixtures and probiotics in order to benefit from their safe and beneficial activity. In particular, it would be desirable to use natural agents to induce a more rapid response from herbal medicines by stimulating their beneficial action. The desirability of a combination of natural agents would be dependent, however, upon the continued absence of adverse side effects. Still further, it would be desirable to enhance the action of pharmaceutical drugs or reduce the likelihood of side effects by joining them with natural agents.

To achieve the foregoing and other objects and in accordance with the purpose of the present invention, as embodied and broadly described herein, the methods and products of this invention may comprise the following.

DISCLOSURE OF INVENTION

Against the described background, it is therefore a general object of the invention to improve the speed with which medicinal preparations act in treating disease. This object is achieved by providing a combination of a medicinal preparation and probiotic micro-organisms. When combined in one preparation, the probiotics cause the medicinal preparation to act at a faster rate, compared to the medicinal preparation without the probiotic.

A more specific object is to improve the speed of herbal medicines by combining beneficial, non-bacteria-inhibiting, natural herbs with beneficial, probiotic micro-organisms.

Another object is to provide herbal formulations that respond synergistically with selected probiotics to improve the speed of treatment An optional object is to develop probiotics using all natural food ingredients without having to use synthetic chemicals, so that they can be blended with herbs and beneficial, health promoting ayurvedic ingredients, which is of benefit in those countries that regulate ayurvedic medicines.

A further object is to enhance herbal drug activity without creating adverse side effects in the patients.

Another optional object is to provide a combination of herbs with specific micro-organisms to treat specific diseases, including formulating herbal compositions to aid in weight loss and dieting.

Still another object is to provide a specific combination of probiotic and synthesized or extracted allopathic drugs to enhance the activity of the drug without increasing adverse side effects.

Another object is to provide beneficial microbial cultures that are synergistic with non-bacteria-inhibiting herbal drug extracts.

Another object is to provide non-pathogenic, non-toxin producing, beneficial probiotic cultures that will synergistically blend with herbs to speed the medicinal activity of the herbs without side effects.

Another object is to provide different herbal and probiotic combinations to treat human conditions such as arthritis, loss of memory, impotency, anemia, and hepatitis with improved speed of results than with herbal treatments, alone, and without adverse side effects.

A further object is to provide all natural, beneficial microbial cultures in live powder forms suited to be easily mixed with pharmaceutical drugs.

Additional objects, advantages and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

According to the invention, a medicinal preparation for treatment of a disease or disorder in humans and animals combines a drug in a dosage sufficient for effective treatment of a disease or disorder, and a viable probiotic in a quantity sufficient to increase the efficacy of the drug. This combination is qualified by the requirement that the drug is not substantially inhibitory to the viability of the probiotic.

The chosen probiotic is a non-pathogenic, non-toxin producing, beneficial microbial culture preparation. The probiotic is mixed with drugs chosen from specific combinations of herbs and synthetic or extracted allopathic, non-bacteria-inhibiting drugs to treat certain diseases more quickly than is achieved with unaided herbs or unaided allopathic drugs, and without adverse side effects.

The invention provides a method of treating a disease or disorder in a human or animal subject. This method provides for administering to a subject in need of treatment the combination of a drug in an effective amount for treating a disease or disorder, and a probiotic in an effective amount for enhancing the effectiveness of the drug. The drug should be of a type that is not substantially inhibitory to the viability of the probiotic.

The drug is selected from the group consisting of pharmaceutical drugs, herbal drugs, allopathic drugs, homeopathic drugs, periodontal drugs, and mixtures of them. The probiotic is selected from the group consisting of non-pathogenic members of genus Lactococcus, Lactobacilius, Pediococcus, Streptococcus, Propionibacterium, Brevibacterium, Penicillium, and Saccharomyces, and mixtures thereof.

The following description serves to explain the principles of invention.

BEST MODE FOR CARRYING OUT THE INVENTION

This invention combines beneficial micro-organisms with drugs of herbal as well as synthesized or extracted origin to produce drug products of greatly enhanced drug values, without inducing adverse side effects. The invention involves two stages of contraction: In the first, drugs are formulated and prepared to cure specific diseases; and in the second drug activity is enhanced by selecting and adding suitable microbial organisms to the drug. The invention is considered to be broadly applicable to pharmacotherapy, which is the treatment of disease through administration of drugs.

The micro-organisms are of a type referred to herein as probiotics, which are non- pathogenic, non-toxin producing, beneficial culture preparations. Most commonly, the probiotics are from the genus Lactococcus, Lactobacillus, Pediococcus, Streptococcus, Propionibacterium, Brevibacterium, Penicillium, and Saccharomyces, or mixtures thereof. One of the important discoveries of this invention is that effective amounts of a probiotic, combined with an effective amount of a drug, tend to enhance the action of the drug on a patient in need of such treatment, resulting in the drug bringing about relief or cure of a disease or disorder more rapidly than if the drug were administered without the probiotic.

Herbal or natural drugs are among the important groups of medicinal preparations whose action is enhanced or speeded by the addition of a probiotic. An herbal or natural drug includes a medicinal preparation administered most commonly in approximately the state or concentration as found in nature, such as by ingesting a leaf, stem, root, flower, seed, yeast, mold, spore, pollen, node, hip, or the like. Most herbal drugs are taken from plants, and a typical definition of an herb might be a flowering plant valued for its medicinal properties. Thus, in a strict sense an herbal drug is of plant origin. For purposes of this invention and convenience of description, the term "herbal drug" will be taken more broadly to include additional substances that might be termed "natural." These cover other natural products derived from animals or animal products, such as from bees or other insects, honey or other insect product or secretion, animal bones, animal horns, secretions, milk, and other natural products. Often an herbal or natural product is physically treated and enhanced, such as by drying, crumbling, grinding, powdering, dissolving in water or alcohol to form a tea or liquor, or otherwise making the product convenient for use and, in some instances, diluting, extracting or mildly concentrating the herbal drug. Notably, extractions may concentrate effective parts of an herbal remedy, but such effective parts nevertheless would be combined with additional, noneffective elements. Thus, the term "herbal" is defined herein to cover products of natural origin, in approximately the concentration as found in nature, and similar variations and modifications, and the like. As an herbal drug is increased in concentration or purity of active principles, the definition of herbal drug moves into the definition of allopathic drug, often with no bright line separating the two.

Probiotics also work with allopathic drugs. Allopathy is the method of treating disease by the use of agents that produce effects different from those of the disease treated. Allopathy is generally considered to be modem medicine, as practiced by medical doctors. Allopathic drugs generally are considered to be pharmaceutical drugs. Listings of such drugs, their formulas, methods of making, requirements, and tests for strength and purity are described in a Pharmacopoeia As previously mentioned, allopathic drugs sometimes are mere extractions or purified versions of herbal drugs, while others may be chemical and biological compositions not otherwise found in nature.

Homeopathy is a variety of medicine that treats disease by drugs given in minute doses, that would produce in a healthy person symptoms similar to those of the disease. The philosophy of administration is different from that of allopathy. However, the substances administered may be, in some cases, similar to dilute versions of herbal or allopathic medicines.

A periodontal drug is a remedy applied to the mouth or gum tissue, such as a toothpaste, tooth powder, or floss. Although such products primarily may serve a cleaning function, their use effectively controls bacteria and decay and prevents various ailments of the mouth and gum. Hence, the term "periodontal drug" will be used to describe them.

An overweight condition can be considered a disease or disorder, since weight problems can arise for many reasons, including disorders of organs or metabolic problems. Thus, diet drugs or weight loss inducing drugs are included in the types of drugs that are enhanced by combination with probiotics.

Although antibiotics are considered a pharmaceutical drug, it appears that at least some antibiotics are excluded from the scope of pharmaceutical drugs, allopathic drugs, herbal drugs, and periodontal drugs for purposes of this invention. It has been found that at least some antibiotics do not gain enhanced activity by combination with probiotics. Such antibiotics are substantially inhibitory to a probiotic. Although the mechanism of the invention has not been discovered with certainty, it appears the probiotic must be viable in order for to realize the enhanced effectiveness of an accompanying drug. Thus, antibiotics are likely to be substantially inhibitory to commonly available probiotics. Accordingly, in order to gain the advantages of this invention when using antibiotics, it is believed the probiotics may require genetic alterations for development of resistant strains of the probiotic.

While the types of drugs with which probiotics work cover a broad range, the dosages of those drugs also can vary considerably. Since the invention provides an improvement in efficacy of drugs, the dosage of known and used drugs can be conventional dosages practiced in pharmacotherapy. The philosophy of each school of medicine, i.e, allopathy vs homeopathy vs herbalism, may influence the selected dosage of a drug and, correspondingly, the effectiveness of treatment. Nevertheless, to the extent that the selected dosage is effective to treat a disease or disorder, that effect should be enhanced by combination with a probiotic. Often a traditionally used effective dose of a drug remains appropriate. Considering that the invention improves effectiveness of drugs, it may be acceptable to reduce traditional dosages of some drugs when they are administered in combination with a probiotic. Thus, the invention finds primary application when a probiotic is combined with a drug in the general range of dosages typically recommended or prescribed by a doctor or practitioner. Some drugs such as herbal drugs might be taken for long term prophylactic effect in a low dosage. Allopathic drugs tend to be taken at a time of direct need and are given in dosages suitable to produce a more rapid or short term effect. Homeopathic drugs are taken in minute dosages, primarily due to the philosophical beliefs behind this type of treatment. Periodontal drugs such a toothpaste are used on an empirical, as-needed basis.

Selection and preparation of drugs:

Herbal drug formulas with specific ingredients and range of ingredients were formulated on the basis of herbal properties. The herbs used in these preparations were cleaned and dried separately. The dried herbs were powdered individually and then sieved. These individual herbal powders were mixed together according to the required weight of each herb in the preparation. In some instances where sterility or bacteriological standards are enforced, the pulverized herbs are mixed, liquefied in water, heated to 120° to 165° F., and then spray dried. Spray drying made them uniform and improved the shelf life of the final preparation. In some instances, the bitterness of the herbs also is greatly reduced upon spray drying. Wherever non-herbal preparations other than probiotics were required, they were prepared separately and were added to the herbal mix. The herbal mixes were capsulated or tableted in the specified amount to administer to patients.

Non-herbal drugs such as allopathic were purchased and were capsulated or tableted with specific probiotic cultures.

A wide variety of herbs were selected and prepared into formulations. The majority of these herbs are found in India, where a Sanskrit name is used as the popular designation. Below are listed Sanskrit names for many of the herbs, a corresponding botanical name where one could be found, the therapeutic function typically attributed to the herb, and an indication of the portion of the plant or other origin for derivation of the active principle. Because the Sanskrit names may be subject to local variations, this information may be used together to better identify each herb.

Aswagandha (*Withania somnifera*)—intended for stimulating central nervous system, active principle in root;
Kapikachu (*Mucuna pruriens*)—sexual stimulant, active principle in seed;
Gokshura (*Tribulus terrestris*)—reduces urinary tract infections, active principle in seed;
Aljuna (*Terminalia aijuna*)—cardiovascular stimulant, active principle in bark;
Kokilaksha (*Astercantha longifolia*)—sexual stimulant, active principle in seed;
Akarakara (*Anacyclus pyrethrum*)—sexual stimulant, active principle in root;
Jatiphala (*Myristica fragans*)—central nervous system stimulant, active principle in seed;
Saffron (*Crocus sativus*)—central nervous system stimulant, active principle in stigma;
Guduchi (*Tinospora cordifolia*)—central nervous system stimulant, active principle in herbal stem;
Yastimadhu (*Glycyrrhiza glabra*)—central nervous system stimulant, active principle in herbal stem;
Shankapusphi (*Convolvulus pluricaulis*)—improves memory, active principle in leaf;
Jatamansi (*Nardostachys jatamansi*)—central nervous system stimulant, active principle in root;
Abhya (*Terminalia chebula*)—general carminative, active principle in seed;
Maricha (*Piper nigrum*)—carminative, active principle in fruit;
Patha (*Cissampelos pareira*)—central nervous system stimulant, active principle in herbal stem;
Vacha (*Acorus calamus*)—improves vocal cords, active principle in fruit;
Sigro (*Moringa oleifera*)—central nervous system stimulant, active principle in fruit;
Brahmi (*Bacopa monniera*)—improves memory, active principle in leaf;
Guggulu (*Commiphera mukul*)—analgesic and also reduces inflammation;
Shunti (*Zingiber officinale*)—carminative, active principle in root;
Kachur (*Curcuma zedoaria*)—carminative;
Erandamula (*Ricinus communis*)—laxative and reduces inflammation, active principle in seed and root;
Punarnava (*Boerhaavia diffusa*)—analgesic and anti-inflammatory properties, active principle in root;

Bhumyamalaki (*Phyllanthus urinaria*)—hepatic stimulant, active principle in seed and leaf;
Chirayata (*Swertia chirata*)—hepatic stimulant, active principle in whole plant;
Haridra (*Curcuma longa*)—hepatic stimulant, active principle in root;
Kumari (*Aloe barbedensis*)—hepatic stimulant, extract;
Saraponkha (*Tephrosia purpurea*)—hepatic stimulant, active principle in flower;
Bringaraja (*Eclipta alba*)—hepatic stimulant, active principle in leaf;
Haritaki (*Terminalia chebula*)—general stimulant, active principle in fruit;
Vibhitaki (*Terminalia belerica*)—general stimulant, active principle in fruit;
Amlaki (*Phyllanthus emblica*)—general stimulant, active principle in fruit;
Shariva (*Hemidesmus indicus*)—blood purifier, active principle in root;
Satauari (*Asparagus racemosus*)—builds blood volume, active principle in root;
Nimba (*Azadirachta indica*)—antiseptic, active principle in leaf;
Eranda Karkati (*Carica papaya*)—improves digestion, active principle in seed;
Chitramula (*Plumbago zeylanica*)—appetizer, active principle in root;
Pippali (*Piper longum*)—appetizer, active principle in bud;
Hingu (*Ferula foetida*)—appetizer, active principle in resin;
Ativisha (*Aconitum heterophyllum*)—appetizer, active principle in root;
Khadira (*Acacia catechu*)—antiseptic and anti-coagulant, active principle in stem bark;
Apamarga (*Achyranthes aspera*)—antiseptic, active principle in root;
Kovidra (*Bauhinia variegata*)—antiseptic, active principle in root;
Daruharidra (*Berberis arisata*)—antiseptic, active principle in root;
Arka (*Calotropis gigantea*)—anticoagulant, active principle in root;
Chitraka (*Plumbago zeylanica*)—carminative, active principle in leaf;
Eranda (*Ricinus communis*)—laxative, active principle in root and stem;
Dhataki (*Woodfordia fruticosa*)—laxative, active principle in seed;
Bilwa (*Aegle marmelos*)—reduces blood sugar, active principle in leaf;
Jarnbu (*Syzygium cumini*)—reduces blood sugar, active principle in seed;
Lasuna (*Ailium sativum*)—hypoglycemic, active principle in seed;
Beejasara (*Pterocarpus marsupium*)—reduces blood sugar, active principle in seed;
Godamar (*Gymnema sylvestre*)—reduces blood sugar, active principle in seed;
Methi (*Trigonella foenum*)—reduces blood cholesterol, reduces obesity, active principle in seed.

Non-herbal ayurvedic ingredients were selected and prepared in formulations with herbs. The following list provides the Sanskrit name of most of these ingredients, followed, where known, by the corresponding botanical name, therapeutic function and other useful notes of value in identifying the ingredient.

Shilajit (Bitumen)—reduces anxiety and tension, an extract or resin;
Dasamula Kwatha Churna—reduces inflammation, active principle in roots;

Shringi Bhasma (a natural chemical from antelope horns)—general stimulant which supplies calcium, active principle in horn;

Mandura Bhasma (ayurvedic natural chemical which supplies iron compounds) —general stimulant;

Kaseesa Bhasma (ayurvedic supplement which supplies ferrous compounds)—general stimulant;

Rasasindhur (a natural compound which supplies iron sulfate)—general stimulant;

Saindhava Lavana (an ayurvedic salt compound)—general stimulant.

In addition, allopathic or pharmaceutical ingredients were selected and used in formulations. The majority of those are listed below by name, followed by its therapeutic function and origin.

Tetracycline (antibiotic)—pharmaceutical preparation clinically used to inhibit pathogenic bacteria, a synthesized or extracted compound;

Nifedapine—pharmaceutical used to reduce hypertension, a chemically synthesized compound;

Atenelol—pharmaceutical preparation clinically used to reduce hypertension, a synthesized compound;

Fungal diastase—pharmaceutical preparation to reduce indigestion, an extracted and purified enzyme;

Papain—pharmaceutical preparation used to reduce indigestion, extracted and purified enzyme;

Simethicone (silica compound)—pharmaceutical preparation used to reduce gassiness, chemically synthesized compound;

Activated charcoal—adsorbs toxins, a purified natural product

Selection and Preparation of probiotics:

The following strains of probiotic micro-organisms were selected and prepared in combination with drugs: *Lactobacillus lactis, Lactobacillus bulgaricus, Lactobacillus acidophilus, Lactobacillus sporogenes, Lactobacillus casei, Lactococcus lactis* var *lactis, Lactococcus lactis* var *cremoris, Lactococcus lactis* var *lactis* ssp *diacetylactis, Streptococcus faecium, Streptococcus thermophilous, Leuconostoc mesenteroides* ssp *cremoris, Pediococcus acidolactici, Pediococcus cerevisiae, Bifidobacterium bifidus, Bifidobacterium longum, Brevibacterium linens, Propionibacterium shermanii, Propionibacterium arabinosum, Penicillium roquefortii, Penicillium camembertii, Saccharomyces cerevisiae.*

These organisms were examined for their biochemical characteristics. The organisms were selected on the basis of their biological properties to blend with the herbal and non-herbal drug preparations. In particular, some were selected because of characteristics that appeared likely to enhance the performance of the drug with which they were to be used. Others were selected for use in combinations, using the multiple mixed strain culture approach to ensure that at least some probiotics remained viable in the patient's system at the point where the drug was taken into the metabolic system. Significant characteristics and often associated therapeutic values of these micro- organisms include the following:

*Lactobacillus acidophilus* produces lactic acid as an end product by utilizing glucose of the lactose molecule. This organism implants in the gastrointestinal tract, especially in the ileum. Acidophilus is acid resistant and bile resistant Consequently, it can survive and tolerate low pH conditions in the stomach and inhibitory effects of bile in the duodenum. Acidophilus can produce non-specific inhibitory compounds that can inhibit pathogenic bacteria. This organism has been reported to reduce serum cholesterol, incidence of colon cancer, bad breath, and pathogenic yeast.

*Lactobacillus bulgaricus* produces lactic acid by utilizing glucose sugar. It has is thought to improve longevity in humans and animals. It is commonly used as a starter culture in the manufacture of yogurt.

*Streptococcus thermophilous* produces lactic acid in the intestinal tract. It grows symbiotically with *Lactobacillus bulgaricus*. It is thought to improve longevity in humans and animals. It is commonly used as a starter culture in the manufacture of yogurt.

*Lactococcus lactis* var *lactis* produces lactic acid and competes with pathogenic bacteria. It produces nisin, which inhibits spoilable type bacteria. Common uses include the manufacture of cheddar and colby cheese and buttermilk. It produces hydrogen peroxide, which is inhibitory to other micro-organisms.

*Lactococcus lactis* var *cremoris* produces diplococci, which inhibits pathogenic and spoilage bacteria. It produces hydrogen peroxide, which is inhibitory to other micro-organisms. This organism is used in the manufacture of cheddar cheese, buttermilk and sour cream.

*Lactococcus lactis* var *lactis* ssp *diacetylactis* is used in the manufacture of buttermilk. The organism utilizes citric acid or citrate to produce the flavor compound, diacetyl, which inhibits gram negative spoilage type organisms such as pseudomonas.

*Bifidobacterium bifidus* implants in the human gastrointestinal tract and is thought to reduce colon cancer. In addition, it has the capacity to reduce pathogenic micro-organisms.

*Leuconostoc mesenteroides* ssp *cremoris* produces the least amount of acid of the selected species. It is useful to ferment citric acid to acetyl methyl carbinol and diacetyl and has the intrinsic ability to inhibit gram negative spoilage type bacteria.

*Brevibacterium linens* is extremely proteolytic because of its proteolytic enzymes. It is surface smear flora in cheese.

*Penicillium roquefortii* and *penicilium camembertii* are used in the manufacture of blue and camembert cheese. They are known for their extremely proteolytic and lipolytic nature.

*Saccharomyces Cerevisiae* ferments glucose to carbon dioxide and ethanol. This yeast metabolizes complex carbohydrates and stimulates gram positive bacteria Propionibacterium (all species) metabolize lactic acid to produce propionic acid, which is inhibitory to unwanted yeast and molds. They also produce acetic acid, which is inhibitory to gram negative spoilage type bacteria and pathogenic bacteria. In cheese, they contribute to Swiss cheese flavor.

*Streptococcus faecium* is known to survive low pH, high pH, high salt, bile salts, and acids. Nutritionally it successfully competes with pathogenic organisms.

*Pediococcus acidolactici* produces lactic acid by fermenting both simple and complex sugars. It inhibits both spoilage type bacteria and pathogenic bacteria.

*Lactobacillus sporogenes* produces spores that survive stomach acids. In the intestinal tract, this organism inhibits pathogenic and spoilable type bacteria.

Lactic acid producing beneficial bacterial cultures to be used in ayurvedic preparations in combination with ayurvedic herbs were prepared as follows:

An antibiotic free, fresh, whole milk or skim milk was heat treated to 170° F. and held at that temperature for 30 min. to one hour. After the heat treatment, it was cooled to 75° to 115° F., depending upon the optimal growth temperature of the micro-organism. The appropriate culture, previously grown in milk, was inoculated into the heat treated and cooled milk and was incubated until pH came down to 5.2 to 5.6. At this stage, the culture was neutraized to pH 6.5 to 7.0 using all natural calcium compounds (chunnas) such as calcium carbonate and calcium oxide. In order to assure sterility, these calcium compounds were reconstituted in water and then heat treated. After neutralization, the milk was incubated further until pH once again came down to 5.2 to 5.5, and it was re-neutralized. This neutralization procedure was repeated several times, until enough bacterial population was obtained. At this stage, the milk was cooled to 40° F. and was mixed with food grade, nonfat dry milk power, which is a pure milk powder free from antibiotics, until it became a doughy mass. The doughy mass was dried at 280 to 37° C., until it became powder. This powder was milled and stored until it was used in the medicinal preparation.

The procedures were designed and selected, in part, to keep the preparations all natural and thereby to conform to ayurvedic drug regulations as found in India. Since lactic acid bacteria are of plant origin and associate with milk, ayurvedic drug standards were further met by growing these bacteria only in wholesome milk, in a preparation termed satksheera. The pH of the satksheera was kept high enough that the milk did not coagulate and turn into curd, as curd would disqualify the preparation from being a satksheera. Maintaining the milk in fluid state to qualify the preparation as a satksheera enabled the ayurvedic herbal preparations to be licensed by ayurvedic drug authorities in India prior to clinical trials. Some organisms could not drop pH below 5.5 to 5.8 even after a prolonged incubation. These organisms were dried without any neutralization.

In an alternate procedure, lactic acid producing bacteria were prepared by reconstituting antibiotic free, spray dried milk powder, having no chemicals or additives added, to 12 to 15% solids. The neutralizations were carried by using ayurvedic chunnas as neutralizers to qualify them for use in ayurvedic preparations. Also, just as in the kosher type of production conditions, the bacterial cultures used in ayurvedic preparations were purified and subcultured three times in heated milk prior to inoculating them into a final milk to manufacture dried cultures. This was done to maintain their all natural status as a satksheera Procedure for preparation of Probiotics used with allopathic drugs:

A bacteriological medium was prepared using food grade ingredients. The ingredients listed in Table A were reconstituted at 5% to 10% solids level, heated to 1700 to 190° F., and held for 30 to 60 minutes. The medium was cooled to 750 to 110° F., inoculated with active cultures, and incubated until the pH came down to 5.8 to 5.0. Then the cultures were neutralized to pH 5.8 to 6.5 using a food grade neutralizer such as ammonia, ammonium hydroxide, sodium hydroxide, potassium hydroxide, or the like. Next, the incubation was continued until pH once again came down to 5.0 to 5.8, and the neutralization step was repeated. The incubation and neutralization steps were repeated until pH no longer could go down or until the energy sources were completely exhausted in the medium. At this stage, the culture was cooled to 40° F. and spun using a bacteriological industrial grade automatic desludging centrifuge. The concentrated cells thus collected were either spray dried, fortified with nonfat dry milk and autolyzed yeast extract solids and oven dried at 28° to 40° C., or freeze dried. Such dried preparation was used in the allopathic preparations. Cultures produced according to this procedure also are suitable for use in countries without ayurvedic drug control restrictions.

TABLE A

Growth medium for growing Probiotic Lactic Acid producing bacteria

| Ingredient | Percentage | Typical Range | Preferred Range |
| --- | --- | --- | --- |
| Sweet Whey | 66.2 | 30–80 | 50–70 |
| Non-Fat Dry Milk | 15 | 5–40 | 10–20 |
| Autolyzed Yeast Extract | 5 | 2.5–7.5 | 4–6 |
| Disodium Phosphate | 4 | 1.0–6.0 | 2–5 |
| Monosodium Phosphate | 2 | 0.5–3.0 | 1.0–2.5 |
| Ferrous Sulphate | 0.1 | 0.01–0.25 | 0.075–0.20 |
| Magnesium Sulfate | 0.1 | 0.01–1.0 | 0.075–0.50 |
| Magnesium Chloride | 0.1 | 0.01–0.15 | 0.075–0.125 |
| Dextrose | 7.5 | 2.5–15 | 5–10 |

Cultures of propionibacterium were grown in food grade sodium lactate broth. The broth first was sterilized at 121° C. for 15 minutes at 15 pounds pressure and then cooled. The cooled, sterilized medium was inoculated with propionibacterium culture and incubated at 21° C. for a period of from one week to 10 days. The incubated culture was mixed with inert carrier such as corn flour or rice flour and dried in an oven at from 280 to 35° C. After it dried, the culture was pulverized and used along with other cultures in the pharmaceutical preparation.

Food grade mold cultures were grown on moistened bread at room temperature. After they were completely grown, they were pulverized and used in pharmaceutical preparations.

Yeast cultures were grown in yeast-extract-fortified whey broth with aeration. After complete growth of the organism, the whey-grown yeast culture was fortified with inert flour, such as corn flour or rice flour, and dried in an oven at from 28° to 35° C. After drying, the fortified culture preparation was pulverized and used as yeast culture. For larger scale production, these cultures can be spun and either spray dried or lyophflized.

Purchased commercial cultures were checked for purity with the aid of microscopy and biochemical characteristics.

The herbal preparations and probiotics thus prepared were carefully blended according to the desired composition of each drug. The combined herbs and probiotics or allopathic and probiotics were placed into combined dosage units, such as by either capsulating or tableting the combined ingredients, which then were submitted for clinical trials. Applicable procedures were strictly followed in order to conform to ayurvedic or allopathic drug regulations. It is equally acceptable to maintain the drug and probiotic in separate dosage units, such as separate tablets or capsules, to be administered substantially together during clinical trials.

The following examples further illustrate the composition, utility, and method of preparing the products of this invention.

EXAMPLE 1

A combined drug having both herbal and probiotic ayurvedic components was formulated to treat tension, anxiety, loss of memory, neurosis, and depression conditions. This ayurvedic drug is referred to herein as Memory Max, which is a trademark for this product. Its component herbs and probiotic bacteria preparations were prepared according to the procedures previously defined. After the herbs and probiotics were mixed, they were capsulated. Each capsule had 475 mg of the active ingredients. Suitable compositions of Memory Max are listed in Table 1.

Food grade *Lactobacillus acidophilus* bacterial culture was used as probiotic. The probiotic was selected on the basis of its biochemical and physiological properties. The choice of this probiotic was favored by its ability to inhibit putrefactive bacteria that produce toxins such as amines, which tend to cause constriction of blood vessels. In addition, acidophilus can survive stomach acid and then create an acidic environment in the gastrointestinal tract. Also, the organism was screened so that it is not inhibited by the herbs used in the formulation.

For purposes of clinical testing, three test compositions were prepared. One was the herbal and probiotic mix mentioned above and termed Memory Max. The second was a similar herbal preparation with the probiotic omitted. The ingredients and quantities of herbs for the second composition were as listed in Table 1. This herbal preparation was capsulated in 435 mg quantity. The third composition was the probiotic, *Lactobacillus acidophilus* culture, with no herbs. It is capsulated using 435 mg of powder per capsule.

These three test compositions were evaluated to study the effect of the probiotic in enhancing the potency of the herbal formulation. Clinical trials were conducted for a period of six months. Participating physicians selected the trial patients based upon the patients need for treatment. The physicians followed uniform test protocols and reported promptly. The trial patients were supplied capsules and instructed to ingest 2 capsules per day. The patients were checked on a monthly basis. The test employed twelve patients divided into three groups of four patients each. Each group received one of the compositions for testing and evaluation. Thus, one group received Memory Max, a second group received probiotic only, and a third group received the herbal preparation, only. The results are presented in Table 2.

TABLE 1

Composition of Memory Max

| | Herbal, Non-Herbal Ayurvedic & Probiotic Ingredients | | | Preferred quantity (mg) per capsule | Typical range (mg) | Preferred range (mg) |
|---|---|---|---|---|---|---|
| | Sanskrit Name | Botanical Name | Applicable Family or Scientific Name | | | |
| Herbs | Guduchi | Tinospora | Menispermaceae | 25 | 15–50 | 20–30 |
| | Aswagandha | *Withania somnifera* | Solanaceae | 30 | 10–40 | 20–30 |
| | Yastimadhu | *Glycyrrhiza glabra* | Legominaceae | 30 | 15–50 | 25–40 |
| | Shankapusphi | *Convolvulus pluricaulis* | Convolvulanceae | 50 | 30–80 | 40–60 |
| | Jatamamsi | *Nardostachys jatamansi* | Velarianceae | 25 | 15–45 | 20–35 |
| | Abhya | *Terminalia chebula* | Combretaceae | 25 | 5–40 | 15–30 |
| | Maricha | *Piper nigrum* | Piperaceae | 25 | 10–50 | 15–30 |
| | Patha | *Cissampelos pareira* | Menispermaceae | 25 | 15–50 | 20–40 |
| | Vacha | *Acorus calamus* | Ataleae | 25 | 5–35 | 20–30 |
| | Sigro | *Mominga oleifera* | Moringaceae | 25 | 10–50 | 20–40 |
| | Brahmi | *Bacopa monnieri* | Scropulariaceae | 75 | 40–100 | 60–80 |
| Non-Herbal Ayurvedics | Shilajit | Bitumen | | 75 | 50–90 | 60–80 |
| Probiotics | | | *Lactobacillus acidophilus* | 40 | 0.1 to 400 | 20–80 |

TABLE 2

Effect of Memory Max, Memory Max minus Probiotic and Probiotic only, on patients with clinical symptoms.

| Variable | Symptoms before treatment | | |
|---|---|---|---|
| | Tension | Loss of Memory | Depression |
| Memory Max (Herbs & Probiotic) | 4 | 3 | 4 |
| Memory Max minus Probiotic (Herbs only) | 4 | 3 | 4 |
| Probiotic only (No herbs) | 4 | 3 | 4 |

| Variable | Symptoms after 1 month of treatment | | | |
|---|---|---|---|---|
| | Tension | Loss of Memory | Depression | Adverse Side Effects |
| Memory Max (Herbs & Probiotic) | 1 | 2 | 1 | ND |
| Memory Max minus Probiotic (Herbs Only) | 4 | 3 | 4 | ND |
| Probiotic Only (No Herbs) | 4 | 3 | 4 | ND |

| Variable | Symptoms after 2 months of treatment | | | |
|---|---|---|---|---|
| | Tension | Loss of Memory | Depression | Adverse Side Effects |
| Memory Max (Herbs & Probiotic) | 1 | 1 | 1 | ND |
| Memory Max minus Probiotic (Herbs Only) | 4 | 3 | 4 | ND |
| Probiotic Only (No Herbs) | 4 | 3 | 4 | ND |

| Variable | Symptoms after 4 months of treatment | | | |
|---|---|---|---|---|
| | Tension | Loss of Memory | Depression | Adverse Side Effects |
| Memory Max (Herbs & Probiotic) | 1 | 1 | 1 | ND |
| Memory Max minus Probiotic (Herbs Only) | 1 | 1 | 2 | ND |
| Probiotic Only (No Herbs) | 3 | 3 | 4 | ND |

| Variable | Symptoms after 6 months of treatment | | | |
|---|---|---|---|---|
| | Tension | Loss of Memory | Depression | Adverse Side Effects |
| Memory Max (Herbs & Probiotic) | 1 | 1 | 1 | ND |
| Memory Max minus Probiotic (Herbs Only) | 1 | 1 | 1 | ND |
| Probiotic Only (No Herbs) | 2 | 3 | 4 | ND |

CODING: 4 = Severe 3 = Modest 2 = Slight 1 = Cured ND = None Detected

The results show that Memory Max, consisting of herbal preparation combined with probiotic, exhibited a pronounced effect in curing the disease in the test patients. Memory Max achieved a cure in about two months, while the herbal preparation accomplished a similar result over a longer period of about 6 months. The probiotic did not have any significant effect in curing these symptoms. However, when the probiotic was introduced together with the herbs in the Memory Max preparation, the beneficial effect was achieved significantly sooner, in about one-third the time. Thus, the clinical trial established that the addition of probiotic to traditional herbal remedy significantly increases the speed of beneficial effect In a separate study varied quantities of *Lactobacillus acidophilus* culture were evaluated for efficiency. It was found that amounts as low as 0.1 mg used with herbs (435 mg), had a pronounced effect in accelerating the beneficial results of herbal activity.

EXAMPLE 2

A probiotic, beneficial microbial culture was added to an herbal remedy formulated to treat symptoms associated with arthritis. This formulation will be referred to as Fleximac, which is a trademark for this preparation. The formulation of Fleximac is detailed in Table 3. The Fleximac was capsulated using 440 mg per capsule. The probiotic, beneficial bacterial cultures used in Fleximac are *Lactobacillus acidophilus* and *Lactobacillus sporogenes*. These were selected in order to create a favorable pH and environmental conditions in the gastrointestinal tract Three formulations were created in order to conduct clinical trials; one consisting of Fleximac, one of the herbal components alone, and one of the probiotic components, alone. Whenever probiotic alone is specified, these two organisms were mixed in equal quantities to arrive at 400 mg per capsule. All three formulations were submitted to physicians for trial on patients in need of treatment to alleviate arthritic symptoms. The patients were instructed to take 2 capsules per day and were checked routinely for a six month period. The results of this experiment are presented in Table 4.

The results indicate that the addition of probiotic, beneficial, non-toxic bacterial cultures to herbal preparations greatly improved the effectiveness of the herbal drug. The herbal preparation alone took six months to alleviate the arthritis symptoms. The probiotic bacterial cultures, alone, did not have any effect on relieving the athritis. The combination of herbs and probiotic bacterial cultures in the Fleximac formula showed a synergistic effect and was able to alleviate some of the symptoms in a one month period. It appears that the addition of a probiotic component to an herbal treatment improves the efficacy of the treatment, at least by producing a result more rapidly that via herbal treatment, alone.

TABLE 3

Composition of Fleximac

Herbal, Non-Herbal Ayurvedic & Probiotic Ingredients

|  | Sanskrit Name | Botanical Name | Applicable Family or Scientific Name | Preferred quantity (mg) per capsule | Typical range (mg) | Preferred range (mg) |
|---|---|---|---|---|---|---|
| Herbs | Guggulu | Commiphera mukul | Burseraceae | 100 | 50–150 | 75–100 |
|  | Shunti | Zingiber ofticinale | Zingiberaceae | 25 | 10–50 | 20–35 |
|  | Kachur | Curuma zedoaria | Zingiberaceae | 25 | 5–60 | 15–40 |
|  | Erandamula | Ricinus communis | Euphorbiaceae | 50 | 30–80 | 40–60 |
|  | Punarnava | Boerhaavia diffusa | Nyctaginaceae | 50 | 20–70 | 30–50 |
|  | Rasna | Pluchea Ianceolata | Asteraceae | 75 | 40–120 | 50–80 |
|  | Kapilu | Strychnos nux vomica | Strychnaceae | 25 | 10–40 | 15–30 |
| Non-Herbal Ayurvedics | Dasamula Kwatha Churna |  |  | 50 | 25–80 | 40–60 |
| Probiotics |  |  | Lactobacillus acidophiius | 20 | 0.1–200 | 10–60 |
|  |  |  | Lactobacillus sporogenes | 20 | 0.1–200 | 10–60 |

TABLE 4

Effect of Fleximac, Fleximac minus Probiotic and Probiotic only, on patients with Arthritis clinical symptoms.

| | Symptoms before treatment | | |
|---|---|---|---|
| Variable | Stiffness | Swelling | Pain |
| Fleximac (Herbs & Probiotic) | 3 | 2 | 3 |
| Fleximac minus Probiotic (Herbs Only) | 3 | 2 | 3 |
| Probiotic Only (No Herbs) | 3 | 2 | 3 |

| | Symptoms after 1 month of treatment | | | |
|---|---|---|---|---|
| Variable | Stiffness | Swelling | Pain | Adverse Side Effects |
| Fleximac (Herbs & Probiotic) | 2 | 1 | 1 | ND |
| Fleximac minus Probiotic (Herbs Only) | 3 | 2 | 3 | ND |
| Probiotic Only (No Herbs) | 3 | 2 | 3 | ND |

| | Symptoms after 2 months of treatment | | | |
|---|---|---|---|---|
| Variable | Stiffness | Swelling | Pain | Adverse Side Effects |
| Fleximac (Herbs & Probiotic) | 1 | 1 | 1 | ND |
| Fleximac minus Probiotic (Herbs Only) | 3 | 2 | 3 | ND |
| Probiotic Only (No Herbs) | 3 | 2 | 3 | ND |

| | Symptoms after 4 months of treatment | | | |
|---|---|---|---|---|
| Variable | Stiffness | Swelling | Pain | Adverse Side Effects |
| Fleximac (Herbs & Probiotic) | 1 | 1 | 1 | ND |
| Fleximac minus Probiotic (Herbs Only) | 2 | 1 | 2 | ND |
| Probiotic Only (No Herbs) | 3 | 2 | 3 | ND |

| | Symptoms after 6 months of treatment | | | |
|---|---|---|---|---|
| Variable | Stiffness | Swelling | Pain | Adverse Side Effects |
| Fleximac (Herbs & Probiotic) | 1 | 1 | 1 | ND |
| Fleximac minus Probiotic (Herbs Only) | 1 | 1 | 1 | ND |
| Probiotic Only (No Herbs) | 3 | 2 | 3 | ND |

CODING: 4 = Severe 3 = Modest 2 = Slight 1 = Cured ND = None Detected

EXAMPLE 3

A probiotic, beneficial microbial culture was added to an herbal remedy formulated to treat symptoms associated with liver disfunction. This formulation will be referred to as Livad, which is a trademark for this preparation. The formulation of Livad is detailed in Table 5. The bacterial culture used in Livad as probiotic is *Lactobacillus*

*sporogenes*, in order to create favorable conditions in the gastrointestinal tract.

For the purpose of clinical trials, three formulations were created, one consisting of Livad, one consisting of the herbal component, alone, and one consisting of the probiotic alone. Livad was packed in 665 mg quantities per capsule. The herbal preparation, without probiotic, was packed in 625 mg quantities per capsule. The probiotic component, *Lactobacillus sporogenes*, was capsulated using 625 mg per capsule. All these three preparations were supplied to physicians for clinical trials on patients in need of treatment. The patients were picked on the basis of having typical hepatitis symptoms. A minimum of four patients were picked as subjects to study each variable. The dosage of each was three capsules per day. The patients were checked periodically for a period of six months. The results are tabulated in Table 6.

The results indicate that probiotic alone did not effectively treat the disease. Consequently, it had to be discontinued after 3 months study. The herbal preparation by itself, without probiotic, took four months to treat the disease. Surprisingly, Livad (a combination of herbal preparation and probiotic) cured the disease symptoms in a one month period, indicating that the probiotic (beneficial bacterial culture) had a synergistic effect on the herbal preparation. Also, none of the three preparations had any adverse side effects on patients. This result is significant in that a natural probiotic, which is not a chemical, showed a significant drug boosting effect when applied to a similarly all natural herbal preparation. The probiotic showed this favorable effect when used in quantities as low 0.01 mg. with 625 mg of herbal preparation. Even the smallest quantity of viable probiotic has a pronounced effect in stimulating the herbal preparation because of the ability of the bacteria to multiply and implant in the gastrointestinal tract.

TABLE 5

Composition of Livad

| | Herbal, Non-Herbal Ayurvedic & Probiotic Ingredients | | | Preferred quantity (mg) per capsule | Typical range (mg) | Preferred range (mg) |
|---|---|---|---|---|---|---|
| | Sanskrit Name | Botanical Name | Applicable Family or Scientific Name | | | |
| Herbs | Bhumyamalaki | *Phyllanthus urinaria* | Euphorbiaceae | 75 | 40–125 | 60–80 |
| | Chirayata | *Swertia chirata* | Gentianaceae | 75 | 30–90 | 70–80 |
| | Punarnava | *Boerhaavia diffusa* | Nyctaginaceae | 50 | 20–70 | 30–60 |
| | Haridra | *Curcuma longa* | Zingeberaceae | 50 | 30–80 | 40–60 |
| | Kumari | *Aloe barbedensis* | Agavaceae | 25 | 15–40 | 20–30 |
| | Saraponkha | *Tephrosia purpurea* | Fabaceae | 50 | 30–100 | 40–70 |
| | Guduchi | *Tinospora cordifolia* | Menispermaceae | 25 | 5–35 | 15–30 |
| | Bringaraja | *Eclipta alba* | Asteraceae | 50 | 35–100 | 40–70 |
| | Haritaki | *Terminalia chebula* | Combretaceae | 25 | 10–40 | 20–30 |
| | Vibhitaki | *Terminalia belerica* | Combretaceae | 25 | 10–40 | 20–30 |
| | Amlaki | *Phyllanthus Emblica* | Euphorbiaceae | 25 | 10–40 | 20–30 |
| Non-Herbal Ayurvedics | Shringi Basma | | | 50 | 30–70 | 40–60 |
| | Mandura Bhasma | | | 50 | 40–80 | 50–60 |
| | Kaseesa Bhasma | | | 50 | 30–70 | 40–60 |
| Probiotics | | *Lactobacillus sporogenes* | | 40 | .01 to 300 | 20–60 |

TABLE 6

Effect of Livad, Livad minus Probiotic and Probiotic only, on patients with clinical symptoms
CODING: 4 = Severe, 3 = Modest, 2 = Slight, 1 = Cured, ND = None Detected, TS = Treatment Stopped

| Variable | Symptoms before treatment: | Symptoms after 1 month of treatment | | Symptoms after 2 months of treatment | | Symptoms after 4 months of treatment | | Symptoms after 6 months of treatment | |
|---|---|---|---|---|---|---|---|---|---|
| | Typical Hepatitis symptoms | Typical Hepatitis symptoms | Adverse side effects | Typical Hepatitis symptoms | Adverse side effects | Typical Hepatitis symptoms | Adverse side effects | Typical Hepatitis symptoms | Adverse side effects |
| Livad (Herbs & Probiotic) | 4 | 1 | ND | 1 | ND | 1 | ND | 1 | ND |
| Livad minus Probiotic (Herbs Only) | 4 | 4 | ND | 2 | ND | 1 | ND | 1 | ND |
| Probiotic only (No Herbs) | 4 | 4 | ND | 4 | ND | TS | | TS | |

EXAMPLE 4

A combined drug having both herbal and ayurvedic probiotic components was formulated to treat the symptoms of anemia This ayurvedic drug is referred to herein as Hemac, which is a trademark for this product. Its component herbs and probiotic bacteria preparations were prepared according to the procedures previously defined. After the herbs and probiotics were mixed, they were capsulated. Suitable compositions of Hemac are listed in Table 7.

Three formulations were compared in order to conduct clinical trials; one consisting of Hemac, one of the herbal components alone, and one of the probiotic components, alone. The herbal preparation served as a negative control. Hemac was packed at 440 mg per capsule, the herbal preparation alone was packed at 400 mg per capsule. The bacterial cultures used in these preparations are *Lactobacillus bulgaricus, Streptococcus thermophilous* and *Lactococcus lactis* var *lactis*. They were chosen to encourage the digestion of lactose in the gastrointestinal tract. The amount of each of these organisms used in Hemac are listed in Table 7. Wherever the probiotics alone were used in clinical studies, the following quantities of each of these organisms were used per capsule: *Lactobacillus bulgaricus*—200 mg; *Streptococcus thermophilous*—100 mg; and *Lactococcus lactis* var *lactis*—100 mg.

The clinical trials were conducted through physicians who selected the patients based upon their need for treatment of anemic condition. The instructed dose of these capsules was two per day. The results of these clinical trials are presented in Table 8.

The results show that the probiotic alone did not have any curative effect on human patients. The herbal preparation without probiotics took about six months to effectively treat the anemia symptoms. The Hemac effectively treated the anemic symptoms in less than two months. It was apparent that probiotics have positive synergistic effect on the beneficial action of herbs. None of the preparations showed adverse side effects.

Hemac was tested on anemic dogs, using a dosage of 1 capsule per day. The results were similarly favorable, indicating that the probiotic fortified ayurvedic herbal drugs can be used in veterinary preparations.

TABLE 7

Composition of Hemac

| | Herbal, Non-Herbal Ayurvedic & Probiotic Ingredients | | | Preferred | | |
|---|---|---|---|---|---|---|
| | Sanskrit Name | Botanical Name | Applicable Family or Scientific Name | quantity (mg) per capsule | Typical range (mg) | Preferred range (mg) |
| Herbs | Shariva | *Hemidesmus indicus* | Asclepidaceae | 50 | 30–100 | 40–70 |
| | Maricha | *Piper nigrum* | Piperaceae | 50 | 35–85 | 30–60 |
| | Satauari | *Asparagus racemosus* | Asperragaceae | 50 | 30–80 | 40–60 |
| | Nimba | *Azadirachta indica* | Meliaceae | 75 | 25–100 | 50–80 |
| Non-Herbal Ayurvedics | Mandura Bhasma | | | 50 | 10–75 | 30–60 |
| | Kaseesa Bhasma | | | 50 | 10–75 | 30–60 |
| | Shringi Bhasma | | | 50 | 30–80 | 40–60 |
| | Rasasindhur | | | 25 | 10–60 | 20–30 |
| Probiotics | | | *Lactobacillus bulgaricus* | 20 | 2.5–100 | 15–50 |
| | | | *Streptococcus thermophilous* | 10 | 1.5–50 | 5–25 |
| | | | | 10 | 1.5–50 | 5–25 |
| | | | *Lactococcus lactis var lactis* | 10 | 5–50 | 7.5–20 |
| | | | | 10 | 5–50 | 75–20 |

TABLE 8

Effect of Hemac, Hemac minus Probiotic and Probiotic only, on patients with Anemic clinical symptoms
CODING: 4 = Severe, 3 = Modest, 2 = Slight, 1 = Cured, ND = None Detected

| Variable | Symptoms before treatment: | Symptoms after 1 month of treatment | | Symptoms after 2 months of treatment | | Symptoms after 4 months of treatment | | Symptoms after 6 months of treatment | |
|---|---|---|---|---|---|---|---|---|---|
| | Anemic symptoms | Anemic symptoms | Adverse side effects | Anemic symptoms | Adverse side effects | Anemic symptoms | Adverse side effects | Anemic symptoms | Adverse side effects |
| Hemac (Herbs & Probiotic) | 3 | 2 | ND | 1 | ND | 1 | ND | 1 | ND |
| Hemac minus Probiotic | 3 | 3 | ND | 3 | ND | 2 | ND | 1 | ND |

TABLE 8-continued

Effect of Hemac, Hemac minus Probiotic and Probiotic only, on patients with Anemic clinical symptoms
CODING: 4 = Severe, 3 = Modest, 2 = Slight, 1 = Cured, ND = None Detected

| Variable | Symptoms before treatment: Anemic symptoms | Symptoms after 1 month of treatment | | Symptoms after 2 months of treatment | | Symptoms after 4 months of treatment | | Symptoms after 6 months of treatment | |
|---|---|---|---|---|---|---|---|---|---|
| | | Anemic symptoms | Adverse side effects | Anemic symptoms | Adverse side effects | Anemic symptoms | Adverse side effects | Anemic symptoms | Adverse side effects |
| (Herbs only) Probiotic only (No Herbs) | 3 | 3 | ND | 3 | ND | 3 | ND | 3 | ND |

EXAMPLE 5

Probiotic, beneficial microbial cultures were added to an herbal remedy formulated to treat symptoms associated with digestive disorders. This formulation will be referred to as DigestoMax, which is a trademark for this preparation. The formulation of DigestoMax is detailed in Table 9.

Three formulations were created in order to conduct clinical trials; one consisting of DigestoMax, one of the herbal components alone, and one of the probiotic components, alone. DigestoMax was packed into 540 mg capsules; the herbs alone, serving as a positive control, were packed into 500 mg capsules. The formula of herbs and quantities of each herb are the same as listed in Table 9. The probiotics alone, serving as a negative control, were used in the following quantities packed into 500 mg capsules: *Penicillium roquefortii*—62.5 mg; *Saccharomyces cerevisiae*—62.5 mg; *Lactobacillus lactis*—125 mg; *Streptococcus faecium*—62.5 mg; *Penicillium camembertii*—62.5 mg; and *Leuconostoc mesenteroides* ssp *cremoris*—125 mg. The probiotics were chosen because they aid in breaking proteins and fats in foods.

The trial was conducted by physicians who also selected the patients on the basis of their need for treatment. They showed digestive disorders such as constipation, general dullness, and irregularities of bowel movement A minimum of four patients were used to check each variable. The patients were instructed to consume the trial capsules at the rate of 2 capsules per day. The clinical trials were carried on for a period of six months. The results are presented in Table 10.

The results show that DigestoMax was more effective than either the herbs alone or probiotic alone. The DigestoMax was effective to treat digestive disorders in one month of use. The herbs alone took about 2 months to treat the disorders. In this example, the probiotics showed a surprising and significant effect in treating the digestive disorders. However, the probiotics took longer than either the DigestoMax or the herbs, i.e. 4 months. This example shows that a definite synergistic effect exists in the action of probiotics with herbs in treating humans. The probiotics have a pronounced effect in enhancing the activity of herbs in humans. None of the preparations exhibited any adverse side effects during the clinical trials.

TABLE 9

Composition of Digest O' Max

| | Herbal, Non-Herbal Ayurvedic & Probiotic Ingredients | | | Preferred quantity (mg) per capsule | Typical range (mg) | Preferred range (mg) |
|---|---|---|---|---|---|---|
| | Sanskrit Name | Botanical Name | Family or Scientific Name | | | |
| Herbs | Eranda Karkati | *Carica papaya* | Caricaceae | 75 | 40–150 | 50–100 |
| | Chitramula | *Plumbago zeylanica* | Plumbaginaceae | 75 | 25–100 | 40–80 |
| | Pippali | *Piper longum* | Piperaceae | 50 | 10–70 | 20–60 |
| | Maricha | *Piper nigrum* | Piperaceae | 50 | 20–80 | 40–60 |
| | Chunti | *Zingeber officinale* | Zingeberaceae | 50 | 20–80 | 40–60 |
| | Hingu | *Ferula foetida* | Apiaceae | 50 | 10–80 | 30–60 |
| | Ativisha | *Aconitum heterophyllum* | Rananuculaceae | 25 | 5–55 | 15–30 |
| Non-Herbal Ayurvedics | Saindhava Lavana | | | 25 | 2.5–35 | 10–30 |
| | Sarjaksheera | | | 50 | 30–80 | 40–80 |
| | Yavakshara | | | 50 | 30–80 | 40–60 |
| Probiotics | | | *Penicillium roquefortii* | 5 | 0.5–30 | 2.5–15 |
| | | | *Penicillium camembertii* | 5 | 0.3–20 | 3–10 |
| | | | *Leuconostoc mesenteroides* ssp *cremoris* | 5 | 0.1–20 | 5–10 |
| | | | *Streptococcus faecium* | 5 | 0.01–10 | 2.5–5 |
| | | | *Brevibacterium linens* | 5 | 0.1–30 | 2.5–10 |
| | | | *Saccharomyces cerevisiae* | 5 | 0.25–30 | 5–20 |

TABLE 10

Effect of DigestoMax, DigestoMax minus Probiotic and Probiotic only, on patients with clinical symptoms Table 10a Symptoms before treatment

| Variable | Constipation | General Condition | Bowel Movement Regularity |
|---|---|---|---|
| DigestoMax (Herbs & Probiotic) | 4 | 3 | 4 |
| DigestoMax minus Probiotic (Herbs Only) | 4 | 3 | 4 |
| Probiotic Only (No Herbs) | 4 | 3 | 4 |

Table 10b

Symptoms after 1 month of treatment

| Variable | Constipation | General Condition | Bowel Movement Regularity | Adverse Side Effects |
|---|---|---|---|---|
| DigestoMax (Herbs & Probiotic) | 1 | 1 | 1 | ND |
| DigestoMax minus Probiotic (Herbs Only) | 2 | 2 | 2 | ND |
| Probiotic Only (No Herbs) | 3 | 2 | 3 | ND |

Table 10c

Symptoms after 2 months of treatment

| Variable | Constipation | General Condition | Bowel Movement Regularity | Adverse Side Effects |
|---|---|---|---|---|
| DigestoMax (Herbs & Probiotic) | 1 | 1 | 1 | ND |
| DigestoMax minus Probiotic (Herbs Only) | 1 | 1 | 1 | ND |
| Probiotic Only (No Herbs) | 2 | 2 | 2 | ND |

Table 10d

Symptoms after 4 months of treatment

| Variable | Constipation | General Condition | Bowel Movement Regularity | Adverse Side Effects |
|---|---|---|---|---|
| DigestoMax (Herbs & Probiotic) | 1 | 1 | 1 | ND |
| DigestoMax minus Probiotic (Herbs Only) | 1 | 1 | 1 | ND |
| Probiotic Only (No Herbs) | 1 | 2 | 1 | ND |

Table 10e

Symptoms after 6 months of treatment

| Variable | Constipation | General Condition | Bowel Movement Regularity | Adverse Side Effects |
|---|---|---|---|---|
| DigestoMax (Herbs & Probiotic) | 1 | 1 | 1 | ND |
| DigestoMax minus Probiotic (Herbs Only) | 1 | 1 | 1 | ND |
| Probiotic Only (No Herbs) | 1 | 2 | 1 | ND |

CODING: 4 = Severe 3 = Modest 2 = Slight 1 = Cured ND = None Detected

DigestoMax was tried on dogs with similar test results. Since the biological make up of many animals is similar, it appeared that any ayurvedic drug that can be used to treat either large or small animals also can be fortified with species specific probiotics to speed up the activity of the herbal drug without causing side effects. Hence, larger doses proportional to body weight were tested in ruminant animals. It was found that DigestoMax is effective in treating animals for digestive conditions such as not eating feed rations and general dullness.

EXAMPLE 6

Probiotics were added to an herbal remedy designed to reduce bleeding and pain of hemorrhoids during defecation. This herbal and probiotic composition is referred to herein as Piloguard, which is a trademark. The preferred composition and ingredients are listed in Table 11, together with several variations.

Three formulations were created in order to conduct clinical trials; one consisting of Piloguard, one consisting of the herbal components alone, and one consisting of the probiotic components, alone. The Piloguard was packed in 540 mg capsules. The herbal fraction, which has the composition listed in a portion of Table 11, was packed in 500 mg capsules. The probiotic component, used as negative control, consisted of the following quantities in formulating a 500 mg capsule: *Pediococcus acidolactici*—125 mg; *Lactobacillus acidophilus*—125 mg; *Bifidobacterium bifidus*—125 mg; and *Lactococcus lactis* var *lactis* ssp *diacetylactis*—125 mg. The *bifidus* and *acidophilus* were chosen in order to create mildly acidic conditions in the intestinal tract, since they tend to implant in the ileum and tend to promote peristalsis.

The trials were conducted by physicians who selected the patients for clinical trials on the basis of severity of symptoms. Each patient was instructed to take 2 capsules per day for a period of six months. The physicians examined the patients periodically and collected the results, which are presented in Table 12.

The Piloguard was effective to treat the hemorrhoids, anal bleeding, and pain in a period of about two months. In contrast, the herbal composition alone was not effective to treat the symptoms completely even after six months treatment. Probiotic by itself did not fully relieve the symptoms; however, a slight improvement was observed with the probiotic only. The herbs, alone, were slightly superior to probiotic alone. However, Piloguard proved to be the best treatment in the shortest time. There appears to be a strong synergistic effect when probiotics are combined with an herbal remedy.

In a separate experiment, it was found that even a trace amount of probiotic (0.05 mg) added to herbs (500 mg) has a significant effect in enhancing the therapeutic effects of the herbs. When large amounts of probiotic were used (300 mg) along with the herbs, the performance was good and still did not produce side effects. It can be concluded that the amount of probiotics can be varied according to the concentration of the bacteria present in a particular probiotic preparation.

TABLE 12

Effect of Piloguard, Piloguard minus Probiotic and Probiotic only, on Patients with clinical symptoms Table 12a

| Variable | Symptoms before treatment | | |
|---|---|---|---|
| | Hemorrhoids | Bleeding | Pain |
| Piloguard (Herbs & Probiotic) | 4 | 3 | 2 |
| Piloguard minus Probiotic (Herbs Only) | 4 | 3 | 3 |
| Probiotic Only (No Herbs) | 4 | 3 | 3 |

Table 12b

| Variable | Symptoms after 1 month of treatment | | | |
|---|---|---|---|---|
| | Hemorrhoids | Bleeding | Pain | Adverse Side Effects |
| Piloguard (Herbs & Probiotic) | 2 | 2 | 2 | ND |
| Piloguard minus Probiotic (Herbs Only) | 4 | 3 | 3 | ND |
| Probiotic Only (No Herbs) | 3 | 2 | 2 | ND |

Table 12c

| Variable | Symptoms after 2 months of treatment | | | |
|---|---|---|---|---|
| | Hemorrhoids | Bleeding | Pain | Adverse Side Effects |
| Piloguard (Herbs & Probiotic) | 1 | 1 | 1 | ND |
| Piloguard minus Probiotic (Herbs Only) | 3 | 2 | 2 | ND |
| Probiotic Only (No Herbs) | 3 | 2 | 2 | ND |

Table 12d

| Variable | Symptoms after 4 months of treatment | | | |
|---|---|---|---|---|
| | Hemorrhoids | Bleeding | Pain | Adverse Side Effects |

TABLE 11

Composition of Piloguard

| | Herbal and Probiotic Ingredients | | | Preferred quantity | | |
|---|---|---|---|---|---|---|
| | Sanskrit Name | Botanical Name | Applicable Family or Scientific Name | (mg) in each capsule | Typical range (mg) | Preferred range (mg) |
| Herbs | Khadira | *Acacia catechu* | Mimsaceae | 50 | 30–100 | 40–60 |
| | Apamarga | *Achyranthes aspera* | Amaranthaceae | 25 | 5–40 | 15–30 |
| | Kumari | *Aloe barbedensis* | Agavaceae | 50 | 10–80 | 30–60 |
| | Kovidra | *Bauhinia variegata* | Caesalpinaceae | 25 | 2.5–35 | 15–30 |
| | Daruharidra | *Berberis arisata* | | 50 | 7.5–65 | 20–55 |
| | Arka | *Calotropis gigantea* | Asclepidiaceae | 50 | 25–85 | 40–70 |
| | Nimba | *Azadirachta indica* | Meliaceae | 50 | 10–100 | 30–80 |
| | Chitraka | *Plumbago zeylanica* | Euphorbiaceae | 50 | 20–70 | 35–60 |
| | Eranda | *Ricinus communis* | Euphorbiaceae | 50 | 30–80 | 40–60 |
| | Dhataki | *Woodfordia fruticosa* | Lythraceae | 50 | 30–80 | 40–60 |
| | Haridra | *Curcuma longa* | Zingeberaceae | 50 | 10–100 | 30–70 |
| Probiotics | | | *Bifidobacterium bifidus* | 10 | 0.1–100 | 10–50 |
| | | | *Pediococcus acidolactici* | 10 | 0.25–75 | 5–50 |
| | | | *Lactobacillus acidophilus* | 10 | 1–50 | 5–30 |
| | | | *Lactococcus lactis* var *lactis* ssp *diacetylactis* | 10 | 1–50 | 5–20 |

TABLE 12-continued

Effect of Piloguard, Piloguard minus Probiotic and Probiotic only, on Patients with clinical symptoms

| Piloguard (Herbs & Probiotic) | 1 | 1 | 1 | ND |
|---|---|---|---|---|
| Piloguard minus Probiotic (Herbs Only) | 2 | 2 | 1 | ND |
| Probiotic Only (No Herbs) | 3 | 2 | 2 | ND |

Table 12e

| Variable | Symptoms after 6 months of treatment ||||
|---|---|---|---|---|
| | Hemor-rhoids | Bleed-ing | Pain | Adverse Side Effects |
| Piloguard (Herbs & Probiotic) | 1 | 1 | 1 | ND |
| Piloguard minus Probiotic (Herbs Only) | 2 | 2 | 1 | ND |
| Probiotic Only (No Herbs) | 3 | 2 | 2 | ND |

CODING: 4 = Severe 3 = Modest 2 = Slight 1 = Cured ND = None Detected

A lower dose of Piloguard was tried on dogs to alleviate anal bleeding and itching during defecation. The Piloguard reduced the disease symptoms. Surprisingly, the dog owners reported that the fecal smell was not putrid during and after the treatment.

EXAMPLE 7

Probiotics were added to an herbal remedy designed to treat symptoms of diabetes. This preparation of herbs and probiotics is referred to herein as Glufac, which is a trademark. The components, their quantities, and variations are listed in Table 13.

Three formulations were created in order to conduct clinical trials; one consisting of Glufac, one consisting of the herbal components, alone, and one consisting of the probiotic components, alone. The Glufac was packed into capsules to arrive at 565 mg per capsule. To check the effect of probiotic only on reducing the symptoms of diabetes, the following quantities of micro-organisms were used to arrive at 525 mg per capsule: Propionibacterium shermanii—131.25 mg; Lactobacillus casei—131.25 mg; Lactobacillus acidophilus—262.50 mg. As a positive control, the herb fraction shown in Table 13 was packed into 525 mg capsules. The probiotic was selected for their ability to implant in the gastrointestinal tract and ferment excess glucose.

Physicians conducted the clinical trials and selected the trial patients based upon need for treatment of typical diabetes symptoms. The clinical trials were conducted for six months. The patients were divided into three groups. Group 1 received Glufac; Group 2 received herbal preparation without probiotic; and Group 3 received probiotic without herbs. The patients were instructed to take three capsules per day. The physicians checked the patients periodically and the recovery results were reported promptly. The results of these clinical trials are presented in Table 14. The probiotic alone showed minimal effect on alleviating the symptoms of diabetes. The herbal preparation alone took six months to treat the diabetes symptoms. The Glufac successfully treated the symptoms of diabetes after two months of treatment The results show that probiotics have a synergistic effect on an herbal remedy, speeding the beneficial activity of herbs. None of the three preparations exhibited adverse side effects. Also none of the herbs in Glufac were inhibitory to the growth of the probiotic organisms.

TABLE 13

Composition of Glufac

| | | Herbal and Probiotic Ingredients ||| Preferred | | |
|---|---|---|---|---|---|---|
| | Sanskrit Name | Botanical Name | Applicable Family or Scientific Name | quantity (mg) in each capsule | Typical range (mg) | Preferred range (mg) |
| Herbs | Bilwa | Aegle marmelos | Rutaceae | 50 | 25–75 | 40–60 |
| | Nimba | Azadirachta indica | Meliaceae | 50 | 30–100 | 40–80 |
| | Guggulu | Commiphera mukul | Borseraceae | 50 | 20–80 | 35–70 |
| | Haridra | Curcuma longa | Zingeberaceae | 50 | 10–70 | 30–60 |
| | Jambu | Syzygium cumini | Mytraceae | 50 | 30–100 | 40–70 |
| | Lasuna | Allium sativum | Alliaceae | 50 | 10–80 | 30–60 |
| | Beejasara | Pterocarpus marsupium | Fabaceae | 50 | 20–60 | 40–50 |
| | Godamar | Gymnema sylvestre | Asclepidiaceae | 25 | 10–50 | 20–35 |
| | Methi | Trigonella foenum | Fabaceae | 75 | 30–100 | 40–80 |
| | Haritaki | Terminalia chebula | Combretaceae | 25 | 10–40 | 20–30 |
| | Vibhitaki | Terminalia belerica | Combretaceae | 25 | 10–40 | 20–30 |
| | Amtaki | Phyllanthus emblica | Euphorbiaceae | 25 | 10–40 | 20–30 |
| Probiotics | | | Propionibacterium shermanii | 10 | 1–75 | 20–50 |
| | | | Lactobacillus casei | 10 | 0.1–80 | 10–40 |
| | | | Lactobacillus acidophilus | 20 | 0.1–100 | 10–50 |

TABLE 14

Effect of Glufac, Glufac minus Probiotic and Probiotic only, on patients with Diabetes clinical symptoms
CODING: 4 = Severe, 3 = Modest, 2 = Slight, 1 = Cured, ND = None Detected

| Variable | Symptoms before treatment | Symptoms after 1 month of treatment | | Symptoms after 2 months of treatment | | Symptoms after 4 months of treatment | | Symptoms after 6 months of treatment | |
|---|---|---|---|---|---|---|---|---|---|
| | Typical Diabetes symptoms | Typical Diabetes symptoms | Adverse side effects | Typical Diabetes symptoms | Adverse side effects | Typical Diabetes symptoms | Adverse side effects | Typical Diabetes symptoms | Adverse side effects |
| Glufac (Herbs & Probiotic) | 3 | 2 | ND | 1 | ND | 1 | ND | 1 | ND |
| Glufac minus Probiotic (Herbs only) | 3 | 3 | ND | 3 | ND | 2 | ND | 1 | ND |
| Probiotic Only (No Herbs) | 3 | 3 | ND | 3 | ND | 3 | ND | 2 | ND |

EXAMPLE 8

Probiotics were added to an herbal remedy for treating impotency. This formula is referred to herein as Libido Max, which is a trademark. The ingredients and variations of formula quantities are presented in Table 15. The herbs selected in this formula were not inhibitory to the microorganisms used in the probiotic fraction. The probiotics were selected for their ability to implant in the gastrointestinal tract and reduce putrefaction and to compete with amine producing bacteria and thus reduce vasoconstriction.

Three formulations were created in order to conduct clinical trials; one consisting of Libido Max, one consisting of the herbal components, alone, and one consisting of the probiotic components, alone. The Libido Max formula was packed into capsules to arrive at 750 mg per capsule. For the sake of clinical studies, the probiotic fraction was packed in 710 mg capsules and included the following quantities of each of the micro-organisms: *Lactobacillus acidophilus*—177.50 mg; *Lactobacillus bulgaricus*—177.50 mg; *Lactobacillus casei*—177.50 mg; and *Lactobacillus sporogenes*—177.50 mg. The formulation of the herbal fraction followed the listing in Table 15 and was capsulated to arrive at 710 mg per capsule.

Physicians conducted the clinical trials and selected the trial patients based upon need for treatment of typical impotency symptoms. The patients were instructed to take the capsules at the rate of 2 capsules per day, two hours before going to bed. The clinical trials were carried on for a six month period. The patients were personally counseled throughout and asked to report any adverse side effects during the trials. The results of this study are presented in Table 16.

The results indicate that Libido Max significantly treated the symptoms. The herbal and probiotic preparation produced improvement in sex drive after the 1st month. By the second month, the herb plus probiotic restored the sex drive. The herbal fraction showed favorable results after a longer time. The probiotic fraction did not show any effect in treating these symptoms. These results show that the herbal preparation in Libido Max, when mixed with probiotics, functions significantly better, apparently due to synergism. It is speculated that the synergism may be caused by action of the micro- organisms in the gastrointestinal tract, where they may create environmental conditions which are conducive for the extraction and absorption of active principles from the herbs. An alternative speculation is that the beneficial bacteria produce a compound or product that interacts with herbs to speed the herbal activity.

TABLE 15

Composition of Libido Max

| | Herbal, Non-Herbal Ayurvedic & Probiotic Ingredients | | | Preferred | | |
|---|---|---|---|---|---|---|
| | Sanskrit Name | Botanical Name | Applicable Family or Scientific Name | quantity (mg) in each capsule | Typical range (mg) | Preferred range (mg) |
| Herbs | Aswagandha | *Withania somnifera* | | 75 | 40–100 | 50–80 |
| | Kapikachu | *Mucuna pruriens* | | 75 | 30–90 | 40–80 |
| | Gokshura | *Tribulus terrestris* | | 50 | 20–80 | 40–60 |
| | Arjuna | *Terminalia arjuna* | | 25 | 10–60 | 20–40 |
| | Kokilaksha | *Astercantha longifolia* | | 50 | 30–70 | 40–60 |
| | Akarakara | *Anacyclus pyrethrum* | | 50 | 30–70 | 40–60 |
| | Jatiphala | *Myristica fragans* | | 50 | 20–80 | 30–70 |
| | Atibala | *Sida cardifolia* | | 50 | 30–70 | 40–60 |
| | Saffron | *Crocus sativus* | | 10 | 2.5–30 | 5–15 |
| Non-Herbal Ayurvedics | Shilajit | Bitumen | | 75 | 30–100 | 50–80 |
| Probiotics | | | *Lactobacillus acidophilus* | 10 | 0.1–100 | 2.5–20 |
| | | | *Lactobacillus bulgaricus* | 10 | 2.5–50 | 5–30 |
| | | | *Lactobacillus casei* | 10 | 2.5–50 | 5–30 |
| | | | *Lactobacilius sporogenes* | 10 | 0.01–50 | 5–30 |

TABLE 16

Effect of Libidomax, Libidomax minus Probiotic and Probiotic only, on patients with clinical symptoms
CODING: 4 = Best, 3 = Average, 2 = Could be better, 1 = Unsatisfactory, ND = None Detected

| Variable | Symptoms before treatment Rating of sex drive | Symptoms after 1 month of treatment | | Symptoms after 2 months of treatment | | Symptoms after 4 months of treatment | | Symptoms after 6 months of treatment | |
|---|---|---|---|---|---|---|---|---|---|
| | | Rating of sex drive | Adverse side effects | Rating of sex drive | Adverse side effects | Rating of sex drive | Adverse side effects | Rating of sex drive | Adverse side effects |
| Libidomax (Herbs & Probiotic) | 1 | 3 | ND | 3 | ND | 4 | ND | 4 | ND |
| Libidomax minus Probiotic (Herbs only) | 1 | 2 | ND | 2 | ND | 3 | ND | 3 | ND |
| Probiotic only (No Herbs) | 1 | 1 | ND | 1 | ND | 1 | ND | 1 | ND |

EXAMPLE 9

Because probiotics appeared to improve the action of a wide variety of herbal remedies, further studies were conducted to evaluate the effect of probiotics in combination with allopathic medicines. It was desired to evaluate the speed of effective treatment and the presence of side effects. Since the probiotics are all natural, it was of particular interest to determine whether the probiotics would have an effect on typical allopathic side effects.

Probiotics were added to an allopathic medicine for reducing dyspepsia or indigestion. The new formula is referred to herein as Prozyme, which is a trademark. Its composition and several variations are listed in Table 17.

Three formulations were created in order to conduct clinical trials; one consisting of Prozyme, one consisting of the allopathic components, alone, and one consisting of the probiotic fraction. The allopathic formulation with probiotic was formulated with the specific quantities presented in Table 19. The tabulated allopathic fraction served as positive control. The tabulated probiotic fraction served as negative control. The probiotics were selected for their ability to implant in the gastrointestinal tract and digest complex sugars such as lactose.

Patients were selected on the basis of dyspepsia symptoms and organized into three groups. Each group was given a different one of the three formulas and instructed to take 1 capsule per day. All the patients were checked periodically for up to 6 months, and the results are tabulated in Table 18.

TABLE 17

Composition of Allopathic Formula with Probiotic (Prozyme) to reduce Dyspepsia

| Allopathic & Probiotic Ingredients | | Preferred quantity | | |
|---|---|---|---|---|
| | Applicable or Scientific Name | (mg) in each capsule | Typical range (mg) | Preferred range (mg) |
| Allopathics | Fungal Diastase | 25 | 10 to 40 | 15 to 30 |
| | Papain | 35 | 20 to 50 | 30 to 40 |
| | Simethicone | 50 | 40 to 80 | 45 to 60 |
| | Activated Charcoal | 75 | 50 to 100 | 60 to 80 |
| Probiotics | Lactobacillus Acidophilus | 40 | 0.1 to 100 | 30 to 50 |
| | Bifidobacterium Bifidus | 20 | 0.25 to 50 | 5 to 30 |
| | Streptococcus Faecium | 20 | 2.0 to 40 | 10 to 30 |

TABLE 18

Effect of Prozyme, Prozyme minus Probiotic and Probiotic only,
on patients with indigestion clinical symptoms Table 18a

| | Symptoms before treatment | |
|---|---|---|
| Variable | Uncomfortable feeling of fullness | Uncomfortable feeling of gassiness |
| Prozyme (Herbs & Probiotic) | 4 | 4 |
| Prozyme minus Probiotic (Herbs | 4 | 4 |

TABLE 18-continued

Effect of Prozyme, Prozyme minus Probiotic and Probiotic only, on patients with indigestion clinical symptoms

| Variable | Uncomfortable feeling of fullness | Uncomfortable feeling of gassiness | Adverse Side Effects |
|---|---|---|---|
| Only) | | | |
| Probiotic Only (No Herbs) | 4 | 4 | |

Table 18b

Symptoms after 1 month of treatment

| Variable | Uncomfortable feeling of fullness | Uncomfortable feeling of gassiness | Adverse Side Effects |
|---|---|---|---|
| Prozyme (Herbs & Probiotic) | 1 | 1 | ND |
| Prozyme minus Probiotic (Herbs Only) | 3 | 4 | ND |
| Probiotic Only (No Herbs) | 4 | 2 | ND |

Table 18c

Symptoms after 2 months of treatment

| Variable | Uncomfortable feeling of fullness | Uncomfortable feeling of gassiness | Adverse Side Effects |
|---|---|---|---|
| Prozyme (Herbs & Probiotic) | 1 | 1 | ND |
| Prozyme minus Probiotic (Herbs Only) | 2 | 3 | ND |
| Probiotic Only (No Herbs) | 4 | 1 | ND |

Table 18d

Symptoms after 4 months of treatment

TABLE 18-continued

Effect of Prozyme, Prozyme minus Probiotic and Probiotic only, on patients with indigestion clinical symptoms

| Variable | Uncomfortable feeling of fullness | Uncomfortable feeling of gassiness | Adverse Side Effects |
|---|---|---|---|
| Prozyme (Herbs & Probiotic) | 1 | 1 | ND |
| Prozyme minus Probiotic (Herbs Only) | 2 | 1 | ND |
| Probiotic Only (No Herbs) | 3 | 1 | ND |

Table 18e

Symptoms after 6 months of treatment

| Variable | Uncomfortable feeling of fullness | Uncomfortable feeling of gassiness | Adverse Side Effects |
|---|---|---|---|
| Prozyme (Herbs & Probiotic) | 1 | 1 | ND |
| Prozyme minus Probiotic (Herbs Only) | 1 | 1 | ND |
| Probiotic Only (No Herbs) | 3 | 1 | ND |

CODING: 4 = Severe  3 = Modest  2 = Slight  1 = Cured  ND = None Detected

These results indicate that the Prozyme—the combined allopathic and probiotic preparation—is more effective than either sub-component, alone. The probiotic exhibited synergistic effect with the allopathic medicine. It appears the combination of probiotics with dyspepsia medicine improves efficiency of the allopathic component without any adverse symptoms. It is speculated that the probiotics may produce favorable acids in the gastrointestinal tract, thereby maintaining a proper pH so that the allopathic drugs will work with improved effectiveness.

EXAMPLE 10

A probiotic was combined with allopathic medicine for reducing blood pressure. This new formulation is referred to herein as Hyperfac, which is a trademark. Its formulation and suggested variations are listed in Table 19.

TABLE 19

Composition of Allopathic Formula with Probiotic (Hyperfac) to reduce hypertension

| Allopathic and Probiotic Ingredients | | Preferred | | |
|---|---|---|---|---|
| | Applicable Pharmaceutical or Scientfic Name | Quantity (mg) in each capsule | Typical range (mg) | Preferred range (mg) |
| Allopathics | Nifedapine | 10 | 5–20 | 7.5–15 |
| | Atenelol | 25 | 20–50 | 25–35 |
| Probiotics | Lactobacillus Acidophilus | 100 | 5–30 | 75–150 |
| | Bifidobacterium Bifidus | 100 | 10–200 20 | 50–150 |

Three formulations were created in order to conduct clinical trials; one consisting of Hyperfac, one consisting of the allopathic components, alone, and one consisting of the probiotic components, alone. The allopathic formulation with probiotic was formulated with the specific quantities presented in Table 19. The tabulated allopathic fraction served as positive control. The tabulated probiotic fraction served as negative control. The probiotics were chosen for their ability to implant in the gastrointestinal tract, create mild acidic conditions, and reduce the number of bacteria producing amines, such as histamine.

Three groups of patients were selected by physicians on the basis of high blood pressure and other symptoms. Each group was given a different one of the three test formulations. The patients were instructed to take 1 capsule per day, and the physicians monitored the test for six months. The test results, consisting of systolic and diastolic blood pressure measurements, are presented in Table 20.

TABLE 20

Effect of Hyperfac, Hyperfac minus Probiotic and Probiotic only, on patients with Hypertension clinical symptoms Table 20a

| Variable | Symptoms before treatment | |
| --- | --- | --- |
| | Range of Systolic Pressure | Range of Diastolic Pressure |
| Hyperfac (Pharmaceutical & Probiotic) | 142–162 | 92–102 |
| Hyperfac minus Probiotic (Pharmaceutical Only) | 138–157 | 88–99 |
| Probiotic Only (No Phamaceuticals) | 140–160 | 91–97 |

Table 20b

| Variable | Symptoms after 1 month of treatment | | |
| --- | --- | --- | --- |
| | Range of Systolic Pressure | Range of Diastolic Pressure | Adverse Side Effects |
| Hyperfac (Pharmaceutical & Probiotic) | 125–136 | 80–88 | ND |
| Hyperfac minus Probiotic (Pharmaceutical Only) | 128–155 | 85–95 | ND |
| Probiotic Only (No Pharmaceutical) | 135–148 | 84–96 | ND |

Table 20c

| Variable | Symptoms after 2 months of treatment | | |
| --- | --- | --- | --- |
| | Range of Systolic Pressure | Range of Diastolic Pressure | Adverse Side Effects |
| Hyperfac (Pharmaceutical & Probiotic) | 128–132 | 82–84 | ND |
| Hyperfac minus Probiotic (Pharmaceutical Only) | 122–155 | 87–95 | ND |

TABLE 20-continued

Effect of Hyperfac, Hyperfac minus Probiotic and Probiotic only, on patients with Hypertension clinical symptoms

| Probiotic Only (No Pharmaceutical) | 131–142 | 85–92 | ND |
| --- | --- | --- | --- |

Table 20d

| Variable | Symptoms after 4 months of treatment | | |
| --- | --- | --- | --- |
| | Range of Systolic Pressure | Range of Diastolic Pressure | Adverse Side Effects |
| Hyperfac (Pharmaceutical & Probiotic) | 122–128 | 77–84 | ND |
| Hyperfac minus Probiotic (Pharmaceutical Only) | 122–128 | 95–92 | ND |
| Probiotic Only (No Pharmaceutical) | 129–144 | 84–92 | ND |

Table 20e

| Variable | Symptoms after 6 months of treatment | | |
| --- | --- | --- | --- |
| | Range of Systolic Pressure | Range of Diastolic Pressure | Adverse Side Effects |
| Hyperfac (Pharmaceutical & Probiotic) | 118–122 | 78–83 | ND |
| Hyperfac minus Probiotic (Pharmaceutical Only) | 125–140 | 82–92 | ND |
| Probiotic Only (No Pharmaceutical) | 130–142 | 85–90 | ND |

CODING: ND = None Detected

The results show that the Hyperfac—allopathic medicine and probiotic —significantly reduced blood pressure in a relatively short time. The allopathic medication, alone, also reduced blood pressure, although requiring a longer time for equivalent results. The probiotic fraction showed a slight effect in reducing blood pressure. These results confirm that probiotics enhance the effect of allopathic drugs. No adverse side effects were observed with any of the drugs during clinical trials. Also, it appears that allopathic drugs are non-inhibitory and do not interfere with the growth of probiotic micro-organisms.

EXAMPLE 11

Probiotic was mixed with antibiotics for general treatment of infection symptoms. The new combination is referred to herein as Bactomac, which is a trademark Tetracycline was selected as a test antibiotic and was mixed with the probiotic micro-organisms according to the formula and quantities listed in Table 21. The probiotics were selected for their ability to create mildly acidic conditions in the gastrointestinal tract and reduce the number of gram negative bacteria.

TABLE 21

Composition of Allopathic Formula with Probiotic (Bactomac) to reduce infection

| Antibiotic and Probiotic Ingredients | | Preferred Quantity (mg) in each capsule | Typical range (mg) | Preferred range (mg) |
|---|---|---|---|---|
| | Applicable Pharmaceutical or Scientific Name | | | |
| Antibiotics | Tetracycline | 500 | 300 to 700 | 450 to 600 |
| Probiotics | *Lactobacillus acidophilus* | 15 | 0.1 to 100 | 5 to 35 |
| | *Streptococcus thermophilous* | 15 | 5 to 75 | 10 to 25 |
| | *Lactobacillus lactis* var *lactis* | 5 | 0.1 to 20 | 2.5 to 10 |
| | *Lactococcus lactis* var *cremoris* | 5 | 0.1 to 20 | 2.5 to 10 |

Three formulations were created in order to conduct clinical trials; one consisting of Bactomac, one consisting of the antibiotic component, alone, and one consisting of the probiotic components, alone. The Bactomac formula of mixed antibiotic and probiotic was packed in capsules to arrive at 540 mg per capsule. The probiotic formula was capsulated to arrive at 500 mg per capsule, using the following components and quantities: *Lactobacillus acidophilus*—150 mg; *Lactobacillus lactis* var *lactis*—150 mg; *Streptococcus thermophilous*—100 mg; and *Lactococcus lactis* var *cremoris*—100 mg. The tetracycline formulation served as positive control and was capsulated at 500 mg per capsule.

Physicians selected the patients for clinical trials on the basis of the following symptoms: sour throat, fever, and general dullness. The clinical trials were conducted for four days. The patients were divided into three groups, and a different one of the three formulations was given to each group. The patients were instructed to take 3 capsules per day, and they were examined on a daily basis. The results of these clinical trials are presented in Table 22.

TABLE 22

Effect of Bactomac, Bactomac minus Probiotic and Probiotic alone, on patients with clinical symptoms
CODING: 4 = Severe, 3 = Modest, 2 = Slight, 1 = Cured, ND = None Detected

| Variable | Symptoms before treatment | | | Symptoms after 4 days of treatment | | | |
|---|---|---|---|---|---|---|---|
| | Sore Throat | Fever | General Dullness | Sore Throat | Fever | General Dullness | Adverse Side Effects |
| Bactomac (Antibiotic and Probiotic) | 4 | 3 | 3 | 1 | 1 | 1 | ND |
| Bactomac with Antibiotic only (no Probiotic) | 4 | 3 | 3 | 1 | 1 | 1 | ND |
| Probiotic only (no Antibiotic) | 4 | 3 | 3 | 3 | 2 | 3 | ND |

The results indicate that the antibiotic completely cured the symptoms after 4 days of treatment. The probiotic did not alleviate the symptoms. The Bactomac, with probiotic and antibiotic, did not exhibit any improvement over the antibiotic alone, indicating that mixing probiotic and antibiotic did not appear to be beneficial. No positive or synergetic effect was observed. Experiments repeated with other antibiotics showed similar result. These results suggest that in order for probiotic to have positive synergistic effect, it must not be mixed with relatively inhibitory components. Thus, herbal drugs or allopathic drugs appear to be the better choices, as compared to antibiotics.

EXAMPLE 12

Probiotics were added to a predominantly herbal preparation for aiding in weight loss. This new formulation is referred to herein as HerboDiet, which is a trademark for this product. Its composition is listed in Table 23. The two herbal ingredients, fennel and fenugreek, are administered in a preferred ratio of approximately 2:1, although variations in this ratio may range to approximately 3:2, as better reflected in the content listings in the table. Mineral supplements, especially of calcium and magnesium salts, are provided to benefit the probiotic. A lipotrophic factor such as lecithin is helpful to prevent absorption of fat. Bulking agents such as cellulose or, as variation in composition, soy okara, help retain water in the gastrointestinal tract An additional helpful addition is a hydrocolloic such as guar gum. The probiotics were chosen for their ability to implant in the gastrointestinal tract and create a mildly acidic environment

TABLE 23

Composition of HerboDiet

| | Common Name | Applicable Latin or Scientific Name | Preferred quantity (%) | Typical Range (%) | Preferred range (%) |
|---|---|---|---|---|---|
| Major Herbs | Fennel | Foeniculum Officinale | 45 | 10–85 | 40–70 |
| | Fenugreek | Trigonella Foenum-Graceum | 22.5 | 5–60 | 20–40 |
| Minor Non-Herbal Food Grade Ingredients | Calcium Carbonate | | 0.5 | 0.1–3.0 | 0.25–2.0 |
| | Magnesium Hydroxide | | 0.5 | 0.1–3.0 | 0.25–2.0 |
| | Magnesium Sulfate | | 0.25 | 0.1–3.0 | 0.20–2.0 |
| | Lecithin | | 2 | 0.5–4.0 | 1–3 |
| | Guar Gum | | 2 | 0.25–7.5 | 1–3 |
| | Pectin | | 2 | 0.17–5.0 | 1–3 |
| | Cellulose | | 21.25 | 5–50 | 10–40 |
| Probiotics | | Lactobacillus acidophilus | 3 | 0.1–10 | 1–5 |
| | | Bifidobacterium bifidus | 1 | 0.01–5 | 0.1–2.5 |

Three formulations were created in order to conduct clinical trials: one consists of HerboDiet according to the formulation of Table 23; the second consists of the HerboDiet formula with elimination of the probiotic portion; and the third consists of the probiotic portion of the HerboDiet formula Trial patients were selected on the basis of their height, weight, and blood cholesterol levels. Four test protocols were established, and one or more patients tested a diet plan according to each protocol. According to a first protocol, the patient was instructed to take the first formulation, HerboDiet, at the rate of 20 grams in the morning, before breakfast, and 20 grams in the evening, before dinner. The HerboDiet was dissolved in a tall glass of water and administered orally. The second protocol called for the patient to take the second formulation, the non-probiotic portions of HerboDiet, at a rate of 4 grams in the morning and 4 grams in the evening, administered by mixing with water. The third protocol similarly required the patient take the protiotic, alone. Under the fourth protocol, the patient received no test formulation. AU patients were instructed to practice diet control and to exercise 10 minutes in the morning and 10 minutes in the evening. Specifically, they were instructed to jog for 8 minutes and run for 2 minutes both in the morning and in the evening. All patient diets were restricted to 1000 to 1300 calories per day, with predominantly protein, moderate amounts of fats and least amount of carbohydrate. Each patient was given one multivitamin and one multi-mineral tablet per day, to maintain their vitamin and mineral balance. The HerboDiet formula optionally may add such vitamins and minerals, which may be added in quantities conforming to recommended daily allowances. The test was conducted over a period of two months. The patients were evaluated at the start and at one month intervals for physical parameters and blood cholesterol level. In addition, they were asked to report any adverse effects in their physical condition. The results are presented in Table 24.

The results indicate HerboDiet was effective to induce significant weight loss and reduction in cholesterol. The patients receiving no test formulation but practicing exercise and diet control lost significantly less weight and realized less reduction in cholesterol over the two month test period. Those taking the non-probiotic, herbal formulation realized intermediate results. The HerboDiet formulation appeared to be most effective, producing beneficial results in the shortest time. It may be noted that the composition of HerboDiet includes not only herbs but also non-herbal food grade ingredients. None of the HerboDiet ingredients are believed to be inhibitory toward probiotics. It appears that probiotics are synergistic when used with herbal as well as non-herbal components, as long as those components are non-inhibitory toward the probiotics.

TABLE 24

Effect of HerboDiet on weight and cholesterol level, with controlled diet and exercise
CODING: ND = None Detected

| | Before treatment | | | After 1 month treatment | | | | After 2 months treatment | | | |
|---|---|---|---|---|---|---|---|---|---|---|---|
| | Weight | Cholesterol | General | Weight | Cholesterol | Adverse | General | Weight | Cholesterol | Adverse | General condition |
| Variable | lbs | mg/deciliter | condition | lbs | mg/deciliter | side | condition | lbs | mg/deciliter | side | |
| HerboDiet | 206 | 262 | below average | 192 | 188 | ND | average | 182 | 164 | ND | above average |
| HerboDiet without Probiotic | 201 | 249 | below average | 192 | 196 | mild constipation | below average | 184 | 187 | mild constipation | average |
| Probiotic alone | 206 | 263 | below average | 201 | 234 | mild constipa | below average | 196 | 213 | mild constipati | below average |
| No medication | 211 | 271 | below average | 205 | 256 | severe constipa | below average | 199 | 251 | severe constipati | below average |

EXAMPLE 13

An ayurvedic formulation using herbs and probiotic was formulated for use as an herbal, all natural tooth powder. This new formulation will be referred to herein as Superb, which is a trademark. Its composition and variations are presented in Table 25. The propionibacteria was selected for its ability to ferment lactic acid to propionic acid, which is a milder acid. Acidophilus is added for its ability to reduce bad breath.

Two test formulations were created in order to conduct clinical trials; one consisting of Superb according to the formulation of Table 25, and the second consisting of the Superb formula with elimination of the probiotic portion, the latter serving as control. These two formulations were tested, respectively, by two groups of patients selected as having bad breath, bleeding gums, and other periodontal disorders. They were instructed to brush twice a day using 5 grams of the assigned formula powder. The test was conducted over a period of six months. Results are summarized in Table 26.

TABLE 25

Composition of Superb (Herbs plus Probiotic)

| Herbal and Probiotic Ingredients | | | Preferred | | |
|---|---|---|---|---|---|
| | Sanskrit Name | Applicable Latin or Scientific Name | quantity (%) per capsule | Typical range (%) | Preferred Range (%) |
| Herbs | Khadira | | 6.75 | 3–15 | 5–12.5 |
| | Shilajit | | 6.75 | 3–15 | 5–12.5 |
| | Guggulu | | 5.40 | 2.5–10 | 4–8 |
| | Arka | | 8.10 | 4.0–16 | 5–10 |
| | Cinchona | | 5.40 | 2.5–12 | 5–8 |
| | Eucalyptus | | 9.45 | 5–15 | 7.5–12 |
| | Vidonga | | 8.10 | 4–12 | 6–10 |
| | Karkata Shringi | | 5.40 | 2.5–10 | 4–8 |
| | Beejasara | | 5.40 | 3–8 | 4–6 |
| | Ardhraka | | 8.20 | 6–12 | 7.5–10 |
| | Amlaki | | 13.51 | 8–22 | 10–15 |
| | Scariva | | 6.75 | 2–12 | 5–7.5 |
| Probiotics | | *Lactobacillus acidophilus* | 4.05 | 0.01–30 | 4–15 |
| | | *Lactobacillus lactis* var *lactis* ssp *diacetylactis* | 3.37 | 0.01–30 | 2.5–12.5 |
| | | *Propionibacterium shermanii* | 3.37 | 0.1–30 | 2.5–15 |

TABLE 26

Effect of Herbs plus Probiotic (Superb) and Herbs only on reducing the periodontal disorders Table 26a Symptoms before treatment

| Variable | Gum Bleeding | Tooth Ache | Bad Breath |
|---|---|---|---|
| Superb (Herbs & Probiotic) | 4 | 4 | 4 |
| Superb minus Probiotic (Herbs Only) | 4 | 4 | 4 |

Table 26b

Symptoms after 1 month of treatment

| Variable | Gum Bleeding | Tooth Ache | Bad Breath | Adverse Side Effects |
|---|---|---|---|---|
| Superb (Herbs & Probiotic) | 3 | 2 | 2 | ND |
| Superb minus Probiotic (Herbs Only) | 3 | 2 | 2 | ND |

Table 26c

Symptoms after 2 months of treatment

| Variable | Gum Bleeding | Tooth Ache | Bad Breath | Adverse Side Effects |
|---|---|---|---|---|
| Superb (Herbs & Probiotic) | 1 | 1 | 1 | ND |
| Superb minus Probiotic (Herbs Only) | 1 | 1 | 2 | ND |

Table 26d

Symptoms after 4 months of treatment

| Variable | Gum Bleeding | Tooth Ache | Bad Breath | Adverse Side Effects |
|---|---|---|---|---|
| Superb (Herbs & Probiotic) | 1 | 1 | 1 | ND |
| Superb minus Probiotic (Herbs Only) | i | 1 | 1 | ND |

Table 26e

Symptoms after 6 months of treatment

| Variable | Gum Bleeding | Tooth Ache | Bad Breath | Adverse Side Effects |
|---|---|---|---|---|
| Superb (Herbs & Probiotic | 1 | 1 | 1 | ND |
| Superb minus Probiotic (Herbs Only) | 1 | 1 | 1 | ND |

CODING: 4 = Severe, 3 = Modest, 2 = Slight, 1 = Cured, ND = None Detected

The results show that both test groups saw improvement in periodontal health within two months. The group using Superb realized a more rapid recovery from bad breath and restoration of sweet breath. Identical conclusions were drawn when the Superb was formulated and used in the form of a toothpaste.

In further tests, a probiotic was added to leading ayurvedic toothpaste, Vicco Vajra Danti, commercially available in India. Vicco Vajra Danti products are manufactured by Vicco laboratories (GOA), Panaji 403001, India Two test formulations were created and evaluated in use by test subjects. In the first formulation, Vicco Vajra Danti toothpaste was fortified by addition of probiotic powder, with 100 mg of probiotic powder sprinkled on 5 grams of the commercial toothpaste. The second formulation consisted of unaltered Vicco Vajra Danti toothpaste and served as control. The results are similar to those obtained in Table 26 and show that the probiotic improves the effectiveness of commercial toothpaste. A like result was obtained by testing a similarly fortified Vicco Vajra Danti dental powder. From all of these tests, it appears that beneficial bacterial cultures enhance the activity of herbs without any side effects.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

We claim:

1. An improved preparation of a drug having a known efficacy at known therapeutic dosage in the treatment of a disease or disorder in humans and animals, wherein the improvement comprises:

a viable probiotic combined with a therapeutic dosage of said drug in a quantity sufficient to increase the known therapeutic efficacy of the drug;

wherein the drug is selected from the group consisting of herbal drugs, allopathic drugs, periodontal drugs, and combinations thereof, but excluding the group consisting of antibiotics, antibodies, and drugs inhibitory to the viability of the probiotic.

2. An improved method of treating a disease or disorder in a human or animal subject by administering to a subject in need of such treatment a drug in a known effective amount for treating the disease or disorder, wherein the improvement comprises:

administering to said subject in need of treatment the combination of:

said drug in known effective amount for treating the disease or disorder; and a probiotic in an effective amount for enhancing the known effectiveness of the drug;

wherein the drug is selected from the group consisting of herbal drugs, allopathic drugs, periodontal drugs, and combinations thereof, but excluding the group consisting of antibiotics, antibodies, and drugs inhibitory to the viability of the probiotic.

3. The preparation of claim 1, wherein said drug comprises an herbal diet aid selected from the group consisting of fennel, fenugreek, and mixtures thereof.

4. The preparation of claim 3, wherein said herbal diet aid comprises a combination of fennel and fenugreek in a ratio in the range from approximately 2:1 to approximately 3:2.

5. The preparation of claim 3, wherein said drug further comprises a vitamin and mineral supplement, a bulking agent, a hydrocolloid, and a lipotrophic factor.

6. The preparation of claim 3, wherein said probiotic is selected from the group consisting of *Lactobacillus acidophilus, Bifidobacterium bifidus*, and mixtures thereof.

7. The preparation of claim 1, wherein said probiotic comprises a non- pathogenic microbial culture.

8. The preparation of claim 1, wherein said probiotic comprises a multiple mixed strain culture.

9. The preparation of claim 1, wherein said probiotic is selected from the group consisting of the genera Lactococcus, Lactobacillus, Pediococcus, Streptococcus, Propionibacterium, Brevibacterium, Penicillium, and Saccharomyces, and mixtures thereof.

10. The preparation of claim 1, wherein said drug is of the type useful in treating a disease or disorder selected from the group consisting of anemia, arthritis, constipation, depression, diabetes, dyspepsia, hemorrhoids, hepatitis, hypertension, impotency, overweight, periodontal disease, and combinations thereof.

11. The preparation of claim 1, wherein said drug is of the type useful in treating a disease or disorder selected from the group consisting of tension, memory loss, joint stiffness, joint pain, swelling, liver disease, rectal bleeding, rectal pain, male impotency, loss of sex drive, high blood cholesterol, bleeding gums, bad breath, tooth ache, digestive disorder, bowel disorder, and combinations thereof.

12. The preparation of claim 1, wherein said drug is selected from the group consisting of toothpaste and tooth powder; and said probiotic is selected from the group consisting of *Lactobacillus acidophilus, Lactobacillus lactis* var *lactis* ssp *diacetylactis, Propionibacterium shermanii*, and combinations thereof.

13. The method of claim 2, wherein said probiotic is selected from the group consisting of non-pathogenic members of the genera Lactococcus, Lactobacillus, Pediococcus, Streptococcus, Propionibacterium, Brevibacterium, Penicillium, and Saccharomyces, and mixtures thereof.

14. The method of claim 2, wherein said drug is an herb, and prior to said step of administering the drug and probiotic, comprising the steps of:

cleaning the herb;

pulverizing the herb; and sieving the herb.

15. The method of claim 14, comprising after sieving said herb and before administering the herb and probiotic, the further steps of:

mixing the sieved herb with water;

liquefying the herb and water mixture;

heat treating the liquified mixture; and drying the mixture.

16. The method of claim 2, wherein comprising prior to said step of administering the drug and probiotic:

first, culturing the probiotic; and second, drying the probiotic culture.

17. The method of claim 15, wherein said step of drying the probiotic culture is by a method selected from the group consisting of spray drying, heat drying, and freeze drying.

18. The method of claim 2, wherein the step of administering said drug and probiotic is preceded by steps comprising:

blending the drug and the probiotic; and forming the mixture into combined dosage units.

19. The method of claim 2, wherein the step of administering said drug and probiotic is performed by simultaneously administering each in separate dosage units.

20. The method of claim 2, wherein said probiotic is administered in a quantity from 0.01% to 90% by weight of the combined drug and probiotic.

* * * * *